(12) United States Patent
Waldhorn et al.

(10) Patent No.: US 11,261,433 B2
(45) Date of Patent: Mar. 1, 2022

(54) AUTOSOMAL-IDENTICAL PLURIPOTENT STEM CELL POPULATIONS HAVING NON-IDENTICAL SEX CHROMOSOMAL COMPOSITION AND USES THEREOF

(71) Applicant: Hadasit Medical Research Services and Development Ltd., Jerusalem (IL)

(72) Inventors: Ithai Waldhorn, Haifa (IL); Benjamin Eithan Reubinoff, Doar-Na HaEla (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 226 days.

(21) Appl. No.: 16/071,094

(22) PCT Filed: Jan. 31, 2017

(86) PCT No.: PCT/IL2017/050111
§ 371 (c)(1),
(2) Date: Jul. 19, 2018

(87) PCT Pub. No.: WO2017/130205
PCT Pub. Date: Aug. 3, 2017

(65) Prior Publication Data
US 2019/0225943 A1 Jul. 25, 2019

Related U.S. Application Data

(60) Provisional application No. 62/289,255, filed on Jan. 31, 2016.

(51) Int. Cl.
*C12N 5/074* (2010.01)
*C12Q 1/02* (2006.01)

(52) U.S. Cl.
CPC ........... *C12N 5/0696* (2013.01); *C12Q 1/025* (2013.01)

(58) Field of Classification Search
CPC .............................. C12N 5/0696; C12Q 1/025
USPC .......................................................... 435/325
See application file for complete search history.

(56) References Cited

U.S. PATENT DOCUMENTS

2014/0371078 A1 12/2014 Abdueva

FOREIGN PATENT DOCUMENTS

| WO | WO 01/42283 | 6/2001 |
| WO | WO 2011/032166 | 3/2011 |
| WO | WO 2011/109612 | 9/2011 |
| WO | WO 2017/130205 | 8/2017 |

OTHER PUBLICATIONS

Office Action dated Dec. 24, 2019 From the Israel Patent Office Re. Application No. 260896 and Its Translation Into English. (7 Pages).
Communication Relating to the Results of the Partial International Search dated Apr. 18, 2017 From the International Searching Authority Re. Application No. PCT/IL2017/050111. (10 Pages).
International Preliminary Report on Patentability dated Aug. 9, 2018 From the International Bureau of WIPO Re. Application No. PCT/IL2017/050111. (12 Pages).
International Search Report and the Written Opinion dated Jun. 7, 2017 From the International Searching Authority Re. Application No. PCT/IL2017/050111. (21 Pages).
Barrett et al. "Reliable Generation of Induced Pluripotent Stem Cells From Human Lymphoblastoid Cell Lines", Stem Cells Translational Medicine, 3(12): 1-6, Published Online Oct. 8, 2014.
Chen et al. "The Number of X Chromosomes Causes Sex Differences in Adiposity in Mice", PLoS Genetics, 8(5): e1002709-1-e1002709-14, May 10, 2012.
Cox et al. "Mouse Model Systems to Study Sex Chromosome Genes and Behavior: Relevance to Humans", Frontiers in Neuroendocrinology, XP055360336, 35(4): 405-419, Oct. 2014. p. 408, Para 2.
Leng et al. "Differentiation of Primordial Germ Cells From Induced Pluripotent Stem Cells of Primary Ovarian Insufficiency", Human Reproduction, XP055361033, 30(3): 737-748, Advance Access Publication Jan. 12, 2015.
Ma et al. "Aberrant Gene Expression Profiles in Pluripotent Stem Cells Induced From Fibroblasts of a Klinefelter Syndrome Patient", The Journal of Biological Chemistry, XP055374776, 287(46): 38970-38979, Nov. 9, 2012. p. 38971, col. 1, Para 2.
Nagata et al. "Perspectives for Induced Pluripotent Stem Cell Technology: New Insights Into Human Physiology Involved in Somatic Mosaicism", Circulation Research, XP055374743, 114(3): 505-510, Jan. 31, 2014. p. 506, Para 1.
Röpke et al. "Sex Chromosomal Mosaicism in the Gonads of Patients With Gonadal Dysgenesis, but Normal Female or Male Karyotypes in Lymphocytes", American Journal of Obstetrics and Gynecology, XP002770384, 190(4): 1059-1062, Apr. 2004. p. 1061, col. 2, Para 2.
Shimizu et al. "Derivation of Integration-Free iPSCs From a Klinefelter Syndrome Patient", Reproductive Medicine and Biology, XP035960656, 15(1): 35-43, Published Online Jul. 3, 2015. p. 36, col. 2, Para 2.
Van Dyke et al. "Testing for Sex Chromosome Mosaicism in Turner Syndrome", International Congress Series, XP055374749, 1298: 9-12, Oct. 1, 2006. p. 11, Para 2, Tables 1, 2.
Communication Pursuant to Article 94(3) EPC dated Apr. 8, 2021 From the European Patent Office Re. Application No. 17707417.6. (10 Pages).
Communication Pursuant to Article 94(3) EPC dated Nov. 11, 2021 From the European Patent Office Re. Application No. 17707417.6. (8 Pages).
Baghbaderani et al. "cGMP-Manufactured Human Induced Pluripotent Stem Cells Are Available for Pre-clinical and Clinical Applications", Stem Cell Reports, 5(4):647-659, XP055857582, Oct. 13, 2015.
Pei et al. "Comparative Neurotoxicity Screening in Human iPSC-Derived Neural Stem Cells, Neurons and Astrocytes", Brain Research, 1638, Part A:57-73, XP029509109, Published Online Aug. 5, 2015.
Romero et al. "A Panel of Induced Pluripotent Stem Ce Is from Chimpanzees: A Resource for Comparative Functional Genomics", eLife. 4: e07103:1-29 ,XP055857580, Published Online Jun. 23, 2015.

*Primary Examiner* — Valarie E Bertoglio

(57) ABSTRACT

An article of manufacture is disclosed which comprises at least two populations of autosomal-identical induced pluripotent stem cells (iPSCs), wherein the complement of sex chromosomes of the first population of the at least two populations is non-identical to the complement of sex chromosomes of the second population of the at least two populations. Uses thereof and methods of generating same are also disclosed.

4 Claims, 12 Drawing Sheets
(10 of 12 Drawing Sheet(s) Filed in Color)

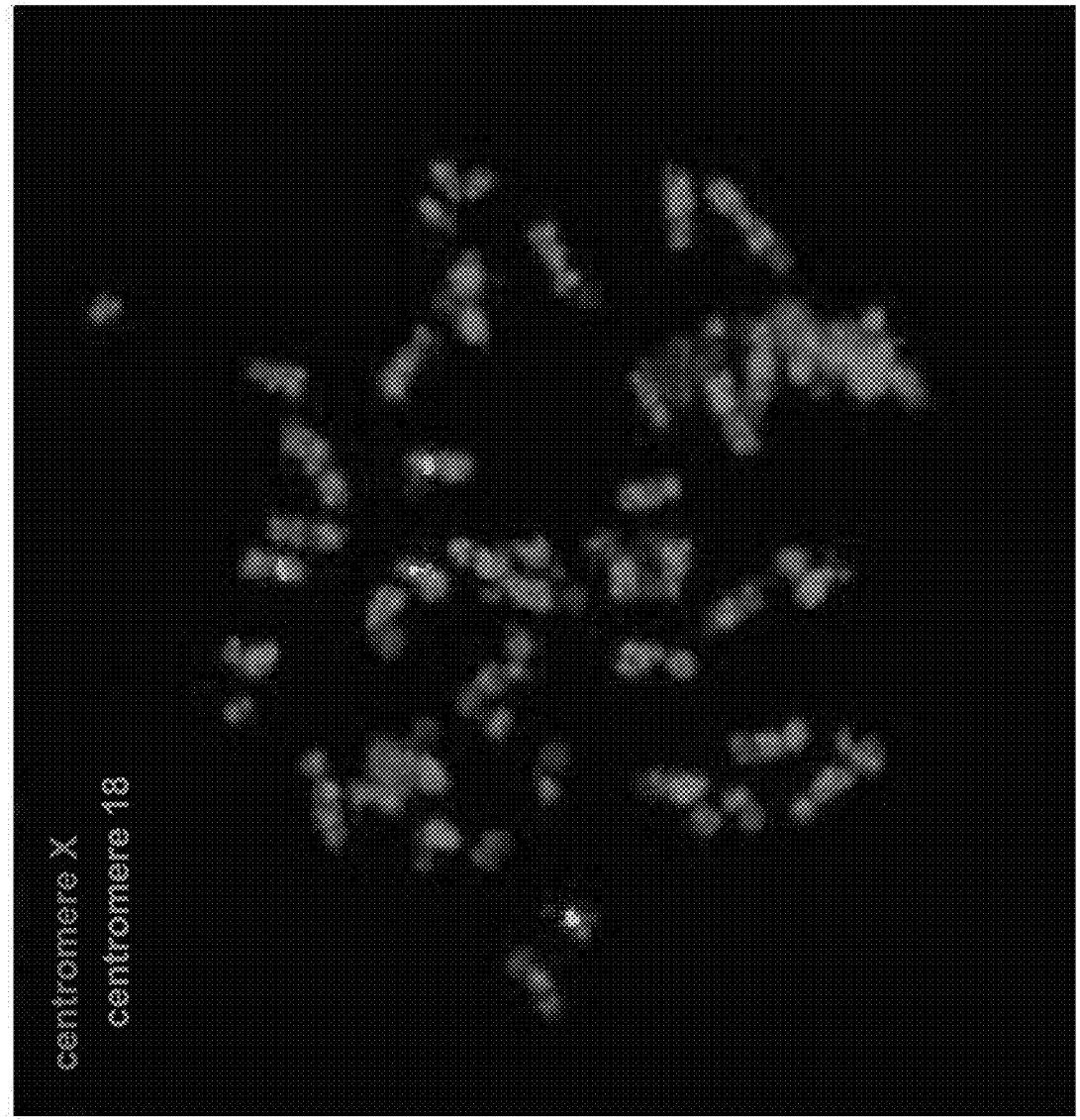

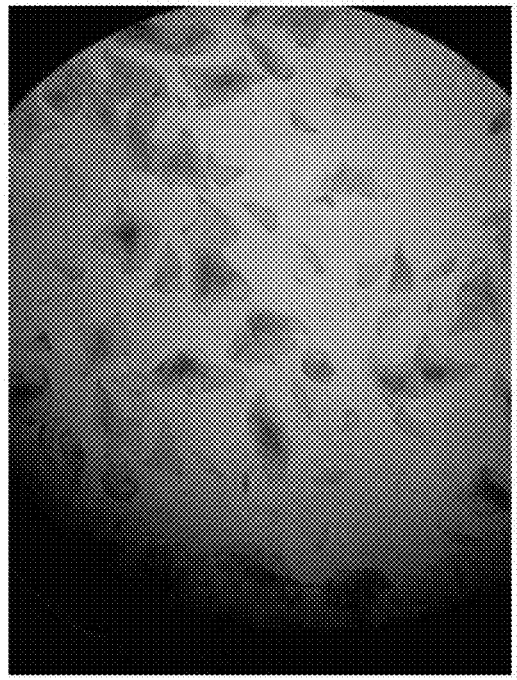
FIG. 4B 63 XO
FIG. 4D 56 XXY
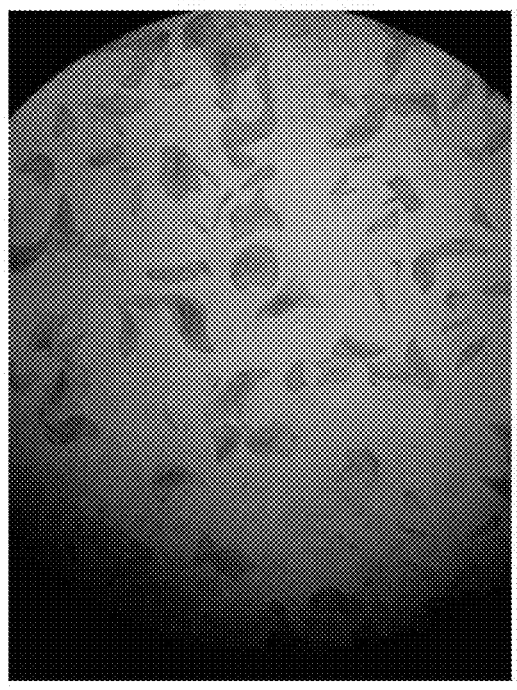
FIG. 4A 59 XY
FIG. 4C 581 XX FIG. 10
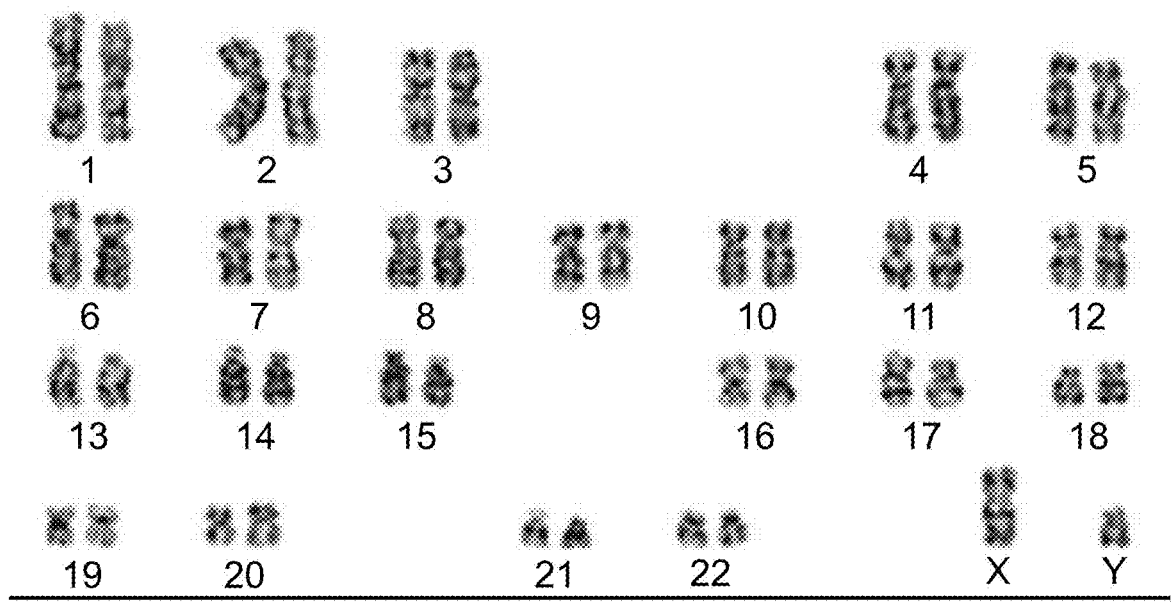
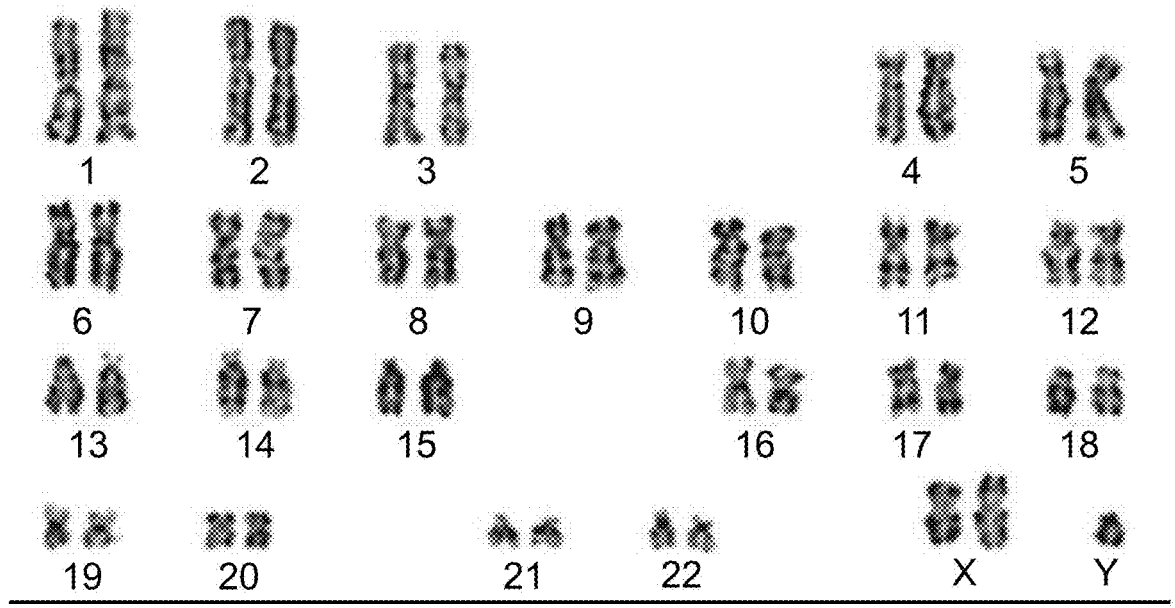

AUTOSOMAL-IDENTICAL PLURIPOTENT STEM CELL POPULATIONS HAVING NON-IDENTICAL SEX CHROMOSOMAL COMPOSITION AND USES THEREOF

RELATED APPLICATIONS

This application is a National Phase of PCT Patent Application No. PCT/IL2017/050111 having International filing date of Jan. 31, 2017, which claims the benefit of priority under 35 USC § 119(e) of U.S. Provisional Patent Application No. 62/289,255 filed on Jan. 31, 2016. The contents of the above applications are all incorporated by reference as if fully set forth herein in their entirety.

FIELD AND BACKGROUND OF THE INVENTION

The present invention, in some embodiments thereof, relates to populations of autosomal-identical pluripotent stem cells having non-identical sex chromosomes.

In recent years, awareness of gender-specific medicine has risen. For example, it is now known that the same medical condition may have different incidence and manifestations in a sex-dependent manner. There are sex-based differences in myocardial infarction prognosis and outcome [1]; different incidence of autoimmune diseases between men and women [2]; and mental disorders such as autism, depression and schizophrenia differ significantly between the sexes in their prevalence, pathophysiology and symptomatology [3-6]. Moreover, drugs may cause different adverse effects in men and women. Between 1997 to 2001, ten prescription drugs were withdrawn by the FDA, eight of which were more dangerous to women than to men [7]. Despite these facts, women are under-represented in clinical trials.

Even though it is unequivocally understood that cell sex influences basic research, cell and animal sex is biased and female animals and cell-lines are a minority. For example, female ESCs have been shown to have a greater capacity to differentiate into muscle [10], neurons are sensitive to cytotoxicity in a sex-dependent manner [11], there is a sexual dimorphism in metabolic profile, and the gene expression of human pluripotent stem cells is sex-dependent [12].

Due to the acknowledged role of sex and gender in medicine, the NIH has required the inclusion of women in NIH-funded clinical research in 1993. In 2014, the NIH enacted a new policy regarding the balance of male and female cells and animals in preclinical studies as well [13].

Sex differences can arise from sex chromosome complement or gonadal hormone effects. For example, the differences in obesity and metabolism between male and female are attributed to the dosage of X chromosome rather than hormonal effect [14]. In order to focus on the role of sex and gender in health and disease, and to distinguish between the hormonal and chromosomal aspects, a suitable model is needed. In mice, two existing models were established in order to address this issue—the four-core-genotype model and the XY* model [15].

Currently, there is no model to address sex and gender differences in humans.

SUMMARY OF THE INVENTION

According to an aspect of some embodiments of the present invention there is provided a method of analyzing the effect of an agent on cells:

(a) exposing a first population of iPS cells to the agent and determining an effect;

(b) exposing a second population of iPS cells to the agent and determining an effect; and (c) comparing the effect of step (a) with the effect of step (b), wherein the first and the second population of iPS cells are autosomal-identical iPSCs, wherein the complement of sex chromosomes of the first population of iPS cells is non-identical to the complement of sex chromosomes of the second population of iPS cells.

According to an aspect of some embodiments of the present invention there is provided a method of analyzing the effect of an agent on cells:

(a) exposing a first population of cells to the agent and determining an effect;

(b) exposing a second population of cells to the agent and determining an effect; and (c) comparing the effect of step (a) with the effect of step (b), wherein the first and the second population of cells are autosomal-identical and differentiated ex vivo from iPSCs derived from a subject having sex chromosome mosaicism, wherein the complement of sex chromosomes of the first population of cells is non-identical to the complement of sex chromosomes of the second population of cells.

According to an aspect of some embodiments of the present invention there is provided an article of manufacture comprising at least two populations of autosomal-identical induced pluripotent stem cells (iPSCs), wherein the complement of sex chromosomes of the first population of the at least two populations is non-identical to the complement of sex chromosomes of the second population of the at least two populations.

According to an aspect of some embodiments of the present invention there is provided an article of manufacture comprising at least two populations of cells being germ cells or of an identical somatic cell type, the at least two populations being autosomal-identical and having been differentiated ex vivo from iPSCs derived from a subject having sex chromosome mosaicism, wherein the complement of sex chromosomes of the first population of the at least two populations is non-identical to the complement of sex chromosomes of the second population of the at least two populations.

According to an aspect of some embodiments of the present invention there is provided a method of preparing iPSCs comprising dedifferentiating somatic cells of a subject having sex chromosome mosaicism under conditions that generate iPSCs, thereby preparing the iPSCs.

According to some embodiments of the invention, the first population has a 46XY karyotype and the second population has a 46XX karyotype.

According to some embodiments of the invention, the second population has a 47XXY karyotype with deletion in a Y specific gene.

According to some embodiments of the invention, the agent is a differentiating agent.

According to some embodiments of the invention, the agent is a pharmaceutical.

According to some embodiments of the invention, the agent is a hormone.

According to some embodiments of the invention, the effect is a toxic effect.

According to some embodiments of the invention, the first population of iPSCs has a 46,XY karyotype and the second population has a 46,XX karyotype.

According to some embodiments of the invention, the second population has a 47XXY karyotype with a deletion in a Y specific gene.

According to some embodiments of the invention, the article of further comprises at least one additional population of autosomal-identical iPSCs, having a karyotype selected from the group consisting of 45X0, 93XXXXY and 47XXY.

According to some embodiments of the invention, the iPSCs are dedifferentiated from blood cells.

According to some embodiments of the invention, the at least two populations of iPSCs express at least one dedifferentiating factor selected from the group consisting of KLF4, c-MYC, OCT4, SOX2, Nanog, and LIN28.

According to some embodiments of the invention, the at least two populations of iPSCs express each of SOX2, OCT4, KLF4 and LIN28.

According to some embodiments of the invention, the iPSCs are derived from a single subject with Kleinefelter Syndrome.

According to some embodiments of the invention, the article of manufacture further comprises germ cells and/or somatic cells differentiated from the first and the second population of iPSCs.

According to some embodiments of the invention, the somatic cells are selected from the group consisting of neuronal cells, cardiac cells, pancreatic cells, hepatic cells, bone cells, muscle cells, fat cells, blood cells and skin cells.

According to some embodiments of the invention, the article of manufacture further comprises a population of iPSCs from which the somatic cells were derived.

According to some embodiments of the invention, the at least two populations of cells are genetically modified to express at least one dedifferentiating factor selected from the group consisting of KLF4, c-MYC, OCT4, SOX2, Nanog, and LIN28.

According to some embodiments of the invention, at least a portion of the cells have a 47XXY karyotype and a portion of the cells have a 46XY karyotype.

According to some embodiments of the invention, the method further comprises downregulating the amount or activity of the Y chromosome of the cells having a 47XXY karyotype.

According to some embodiments of the invention, the downregulating is effected prior to the dedifferentiating.

According to some embodiments of the invention, the downregulating is effected following the dedifferentiating.

According to some embodiments of the invention, the method further comprises culturing the iPSCs.

According to some embodiments of the invention, the method further comprises generating single cell colonies of the iPSCs.

According to some embodiments of the invention, the method further comprises analyzing the sex of the iPSCs of the single cell colonies.

According to some embodiments of the invention, the method further comprises analyzing the karyotype of the iPSCs of the single cell colonies.

According to some embodiments of the invention, the somatic cells comprise blood cells.

According to some embodiments of the invention, the dedifferentiating is effected by expressing in the somatic cells at least one dedifferentiating factor selected from the group consisting of KLF4, c-MYC, OCT4, SOX2, Nanog, and LIN28.

According to some embodiments of the invention, the dedifferentiating is effected by expressing in the somatic cells each of SOX2, OCT4, KLF4 and LIN28.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
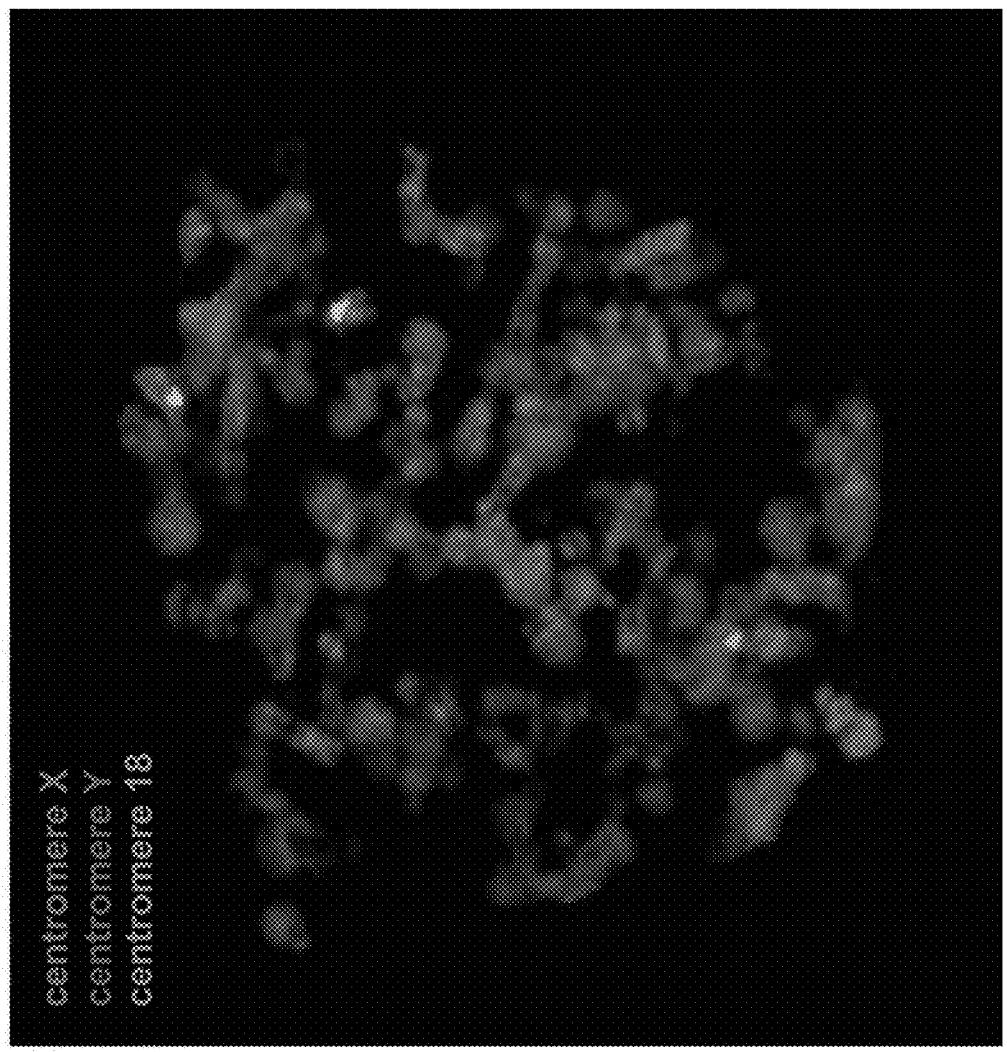
Figure 1B:
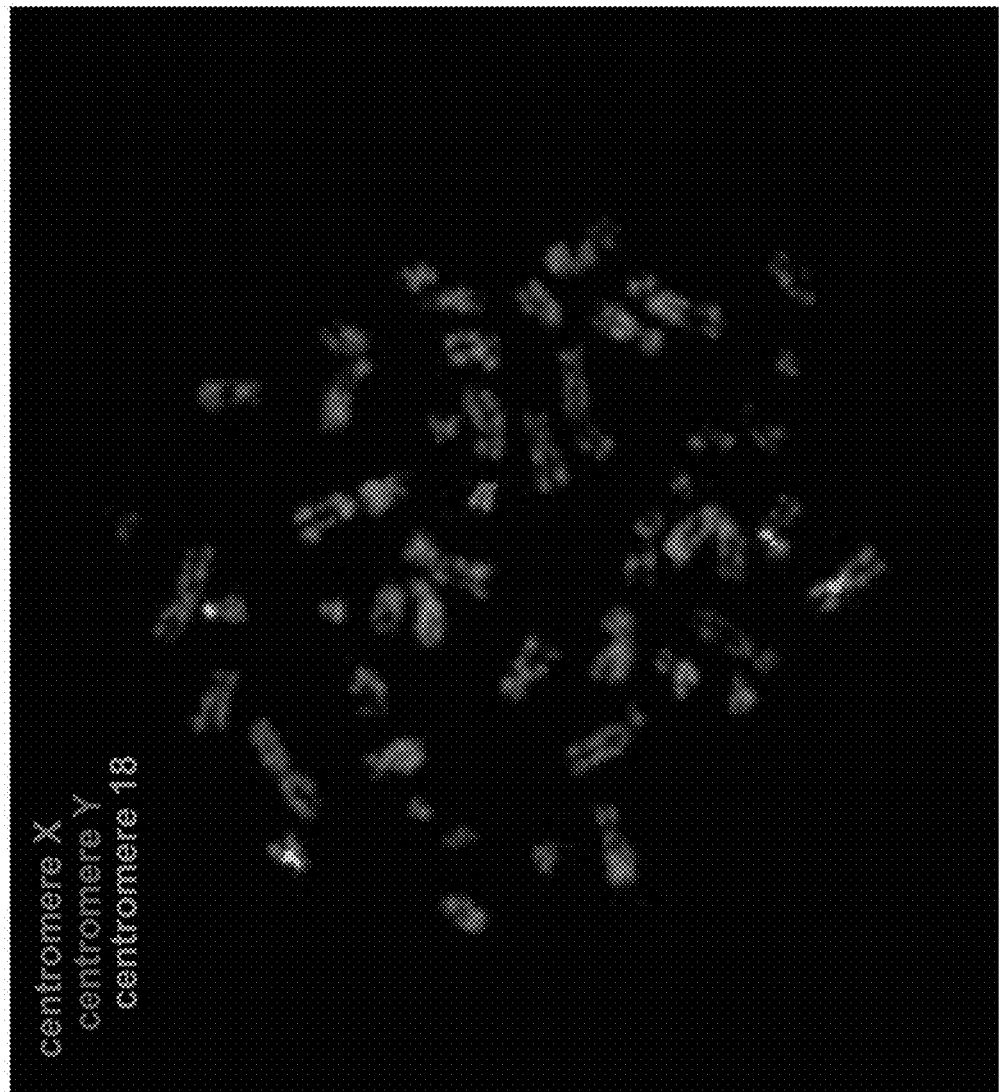

FIGS. 1A-C are photographs of exemplary B cells from the GM17906 cell line following FISH analysis for X (green) and Y (red) chromosomes. Chromosome 18 (Blue) was used as a control. (A) A cell with X and Y chromosomes. (B) A cell with two X and a Y chromosome.

Figure 2:
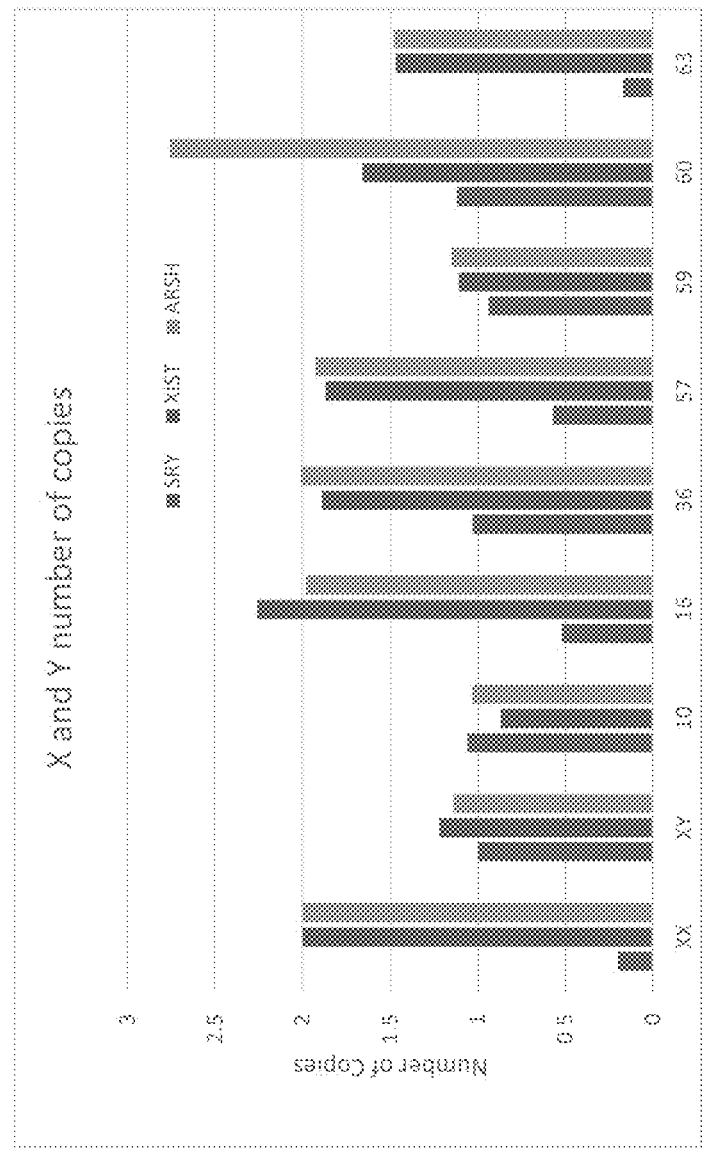

FIG. 2 is a bar graph of copy number variation assay determining the number of X and Y chromosomes in iPSCs clones generated from the GM17906 cell line.

Figure 3:
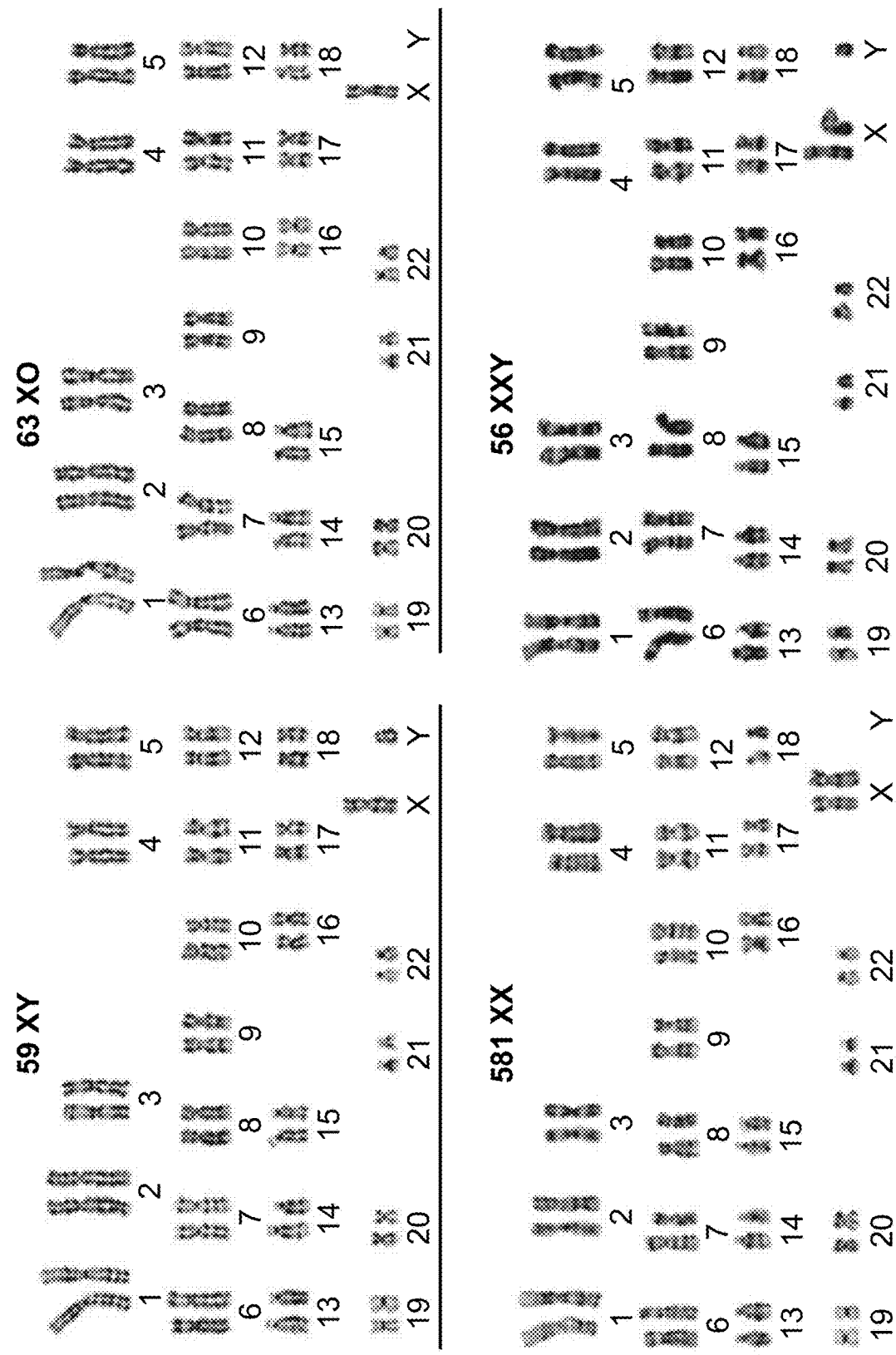

FIG. 3 illustrates typical karyotype results of cells of the present invention—Karyotype of clones #59(46,XY), #63 (45,X0), #581(46,XX), #56(47,XXY). For each clone, ten cells were fully analyzed and in ten cells the chromosomes were counted.

FIGS. 4A-D are photographs of cells of the present invention following an assay of alkaline phosphatase activity—red cells express alkaline phosphatase.

Figure 5:
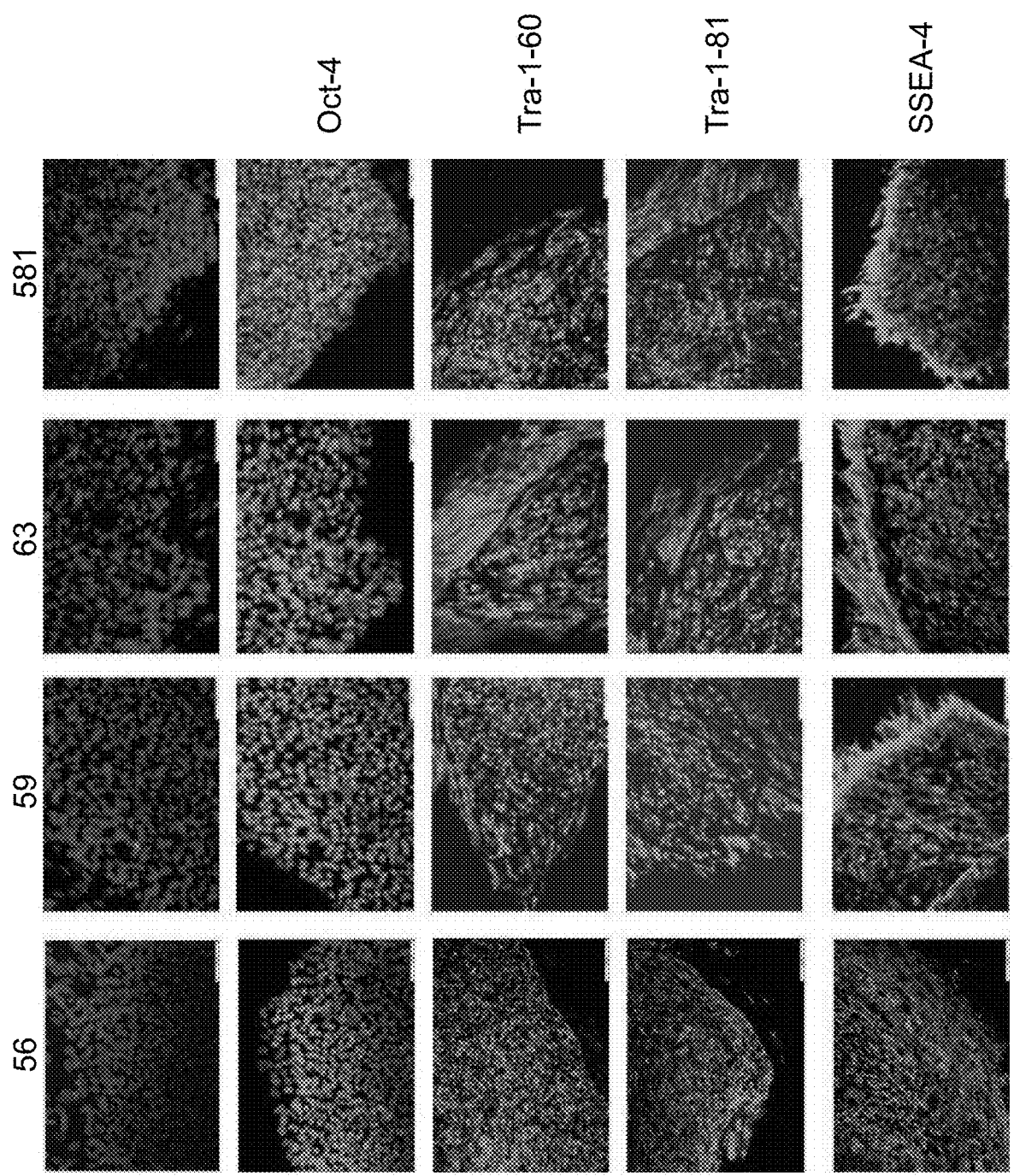

FIG. 5 are photomicrographs illustrating immunofluorescence for pluripotency markers in the cells of the present invention—The pluripotency markers OCT4, Tra-1-60, Tra-1-81, SSEA-4 were stained (green). OCT4 is a nuclear protein while the rest are cytoplasmatic. Cells were counterstained with DAPI (blue).

Figure 6:
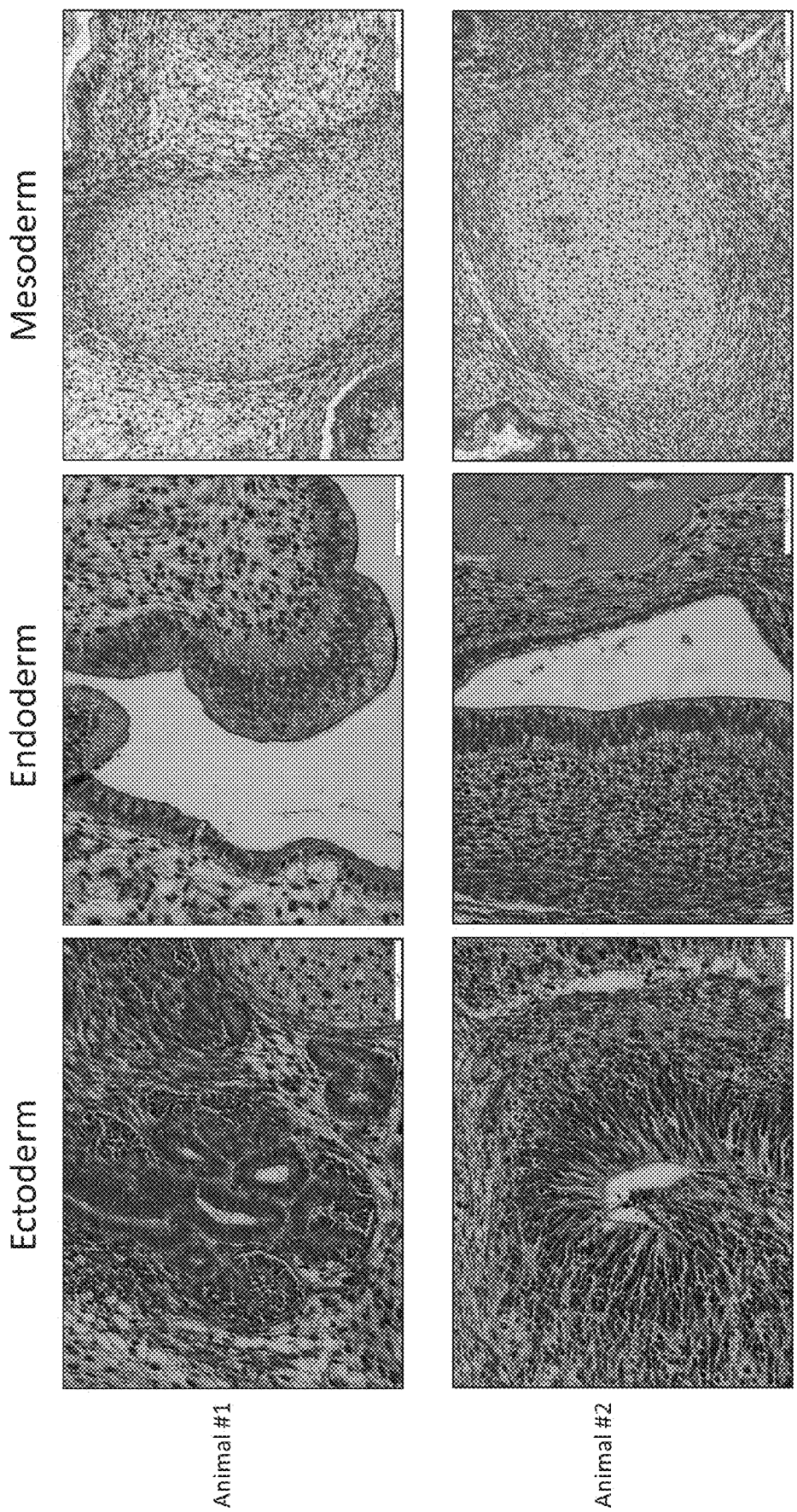

FIG. 6 are photomicrographs illustrating in-vivo differentiation within teratoma tumors—After transplanting #56 cells (47,XXY) subcutaneously, the cells differentiated in teratomas into progeny representing the three germ layers. Hematoxylin-eosin stained histological sections showing neural rosettes (ectoderm), cartilage (mesoderm) and villi structures with columnar glandular epithelium (endoderm).

Figure 7:
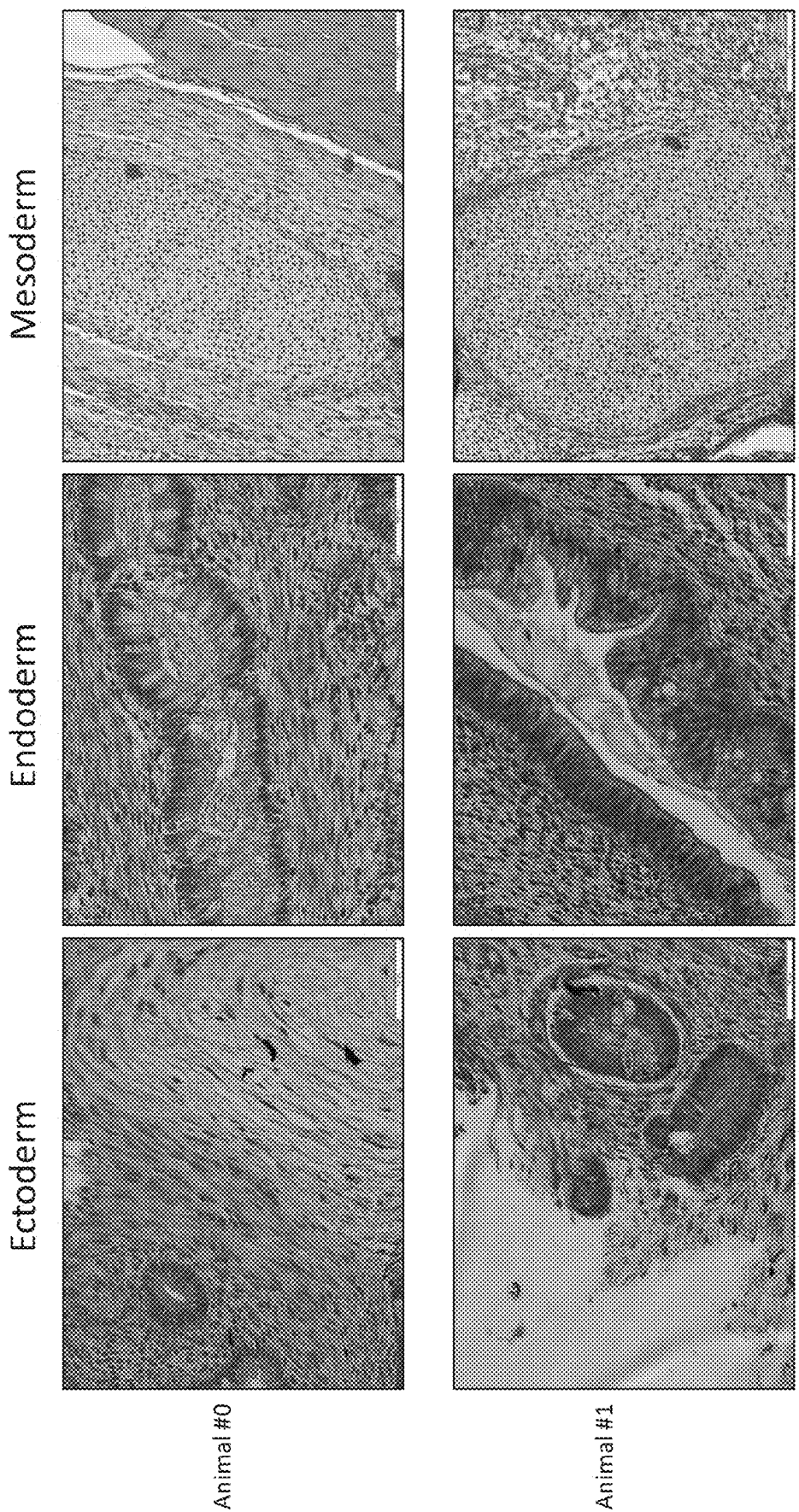

FIG. 7 are photomicrographs illustrating in-vivo differentiation within teratoma tumors—After transplanting #59 (46,XY) cells subcutaneously, the cells differentiated in teratomas into progeny representing the three germ layers. Hematoxylin-eosin stained histological sections showing neural rosettes (ectoderm), cartilage (mesoderm) and villi structures with columnar glandular epithelium (endoderm).

Figure 8:
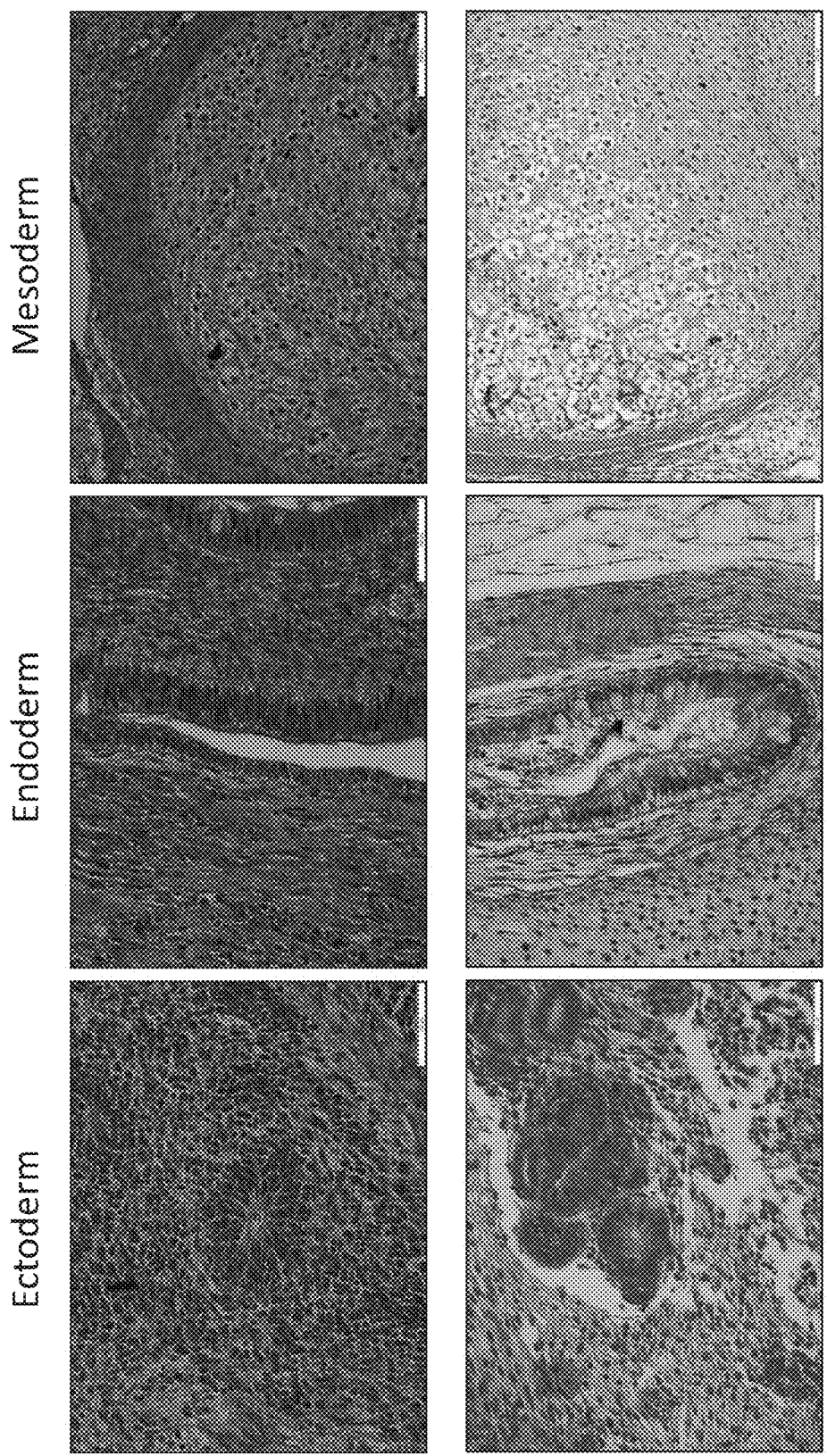

FIG. 8 are photomicrographs illustrating in-vivo differentiation within teratoma tumors After transplanting #63 (45,X0) cells subcutaneously, the cells differentiated in teratomas into progeny representing the three germ layers. Hematoxylin-eosin stained histological sections showing neural rosettes (ectoderm), cartilage (mesoderm) and villi structures with columnar glandular epithelium (endoderm).

Figure 9:
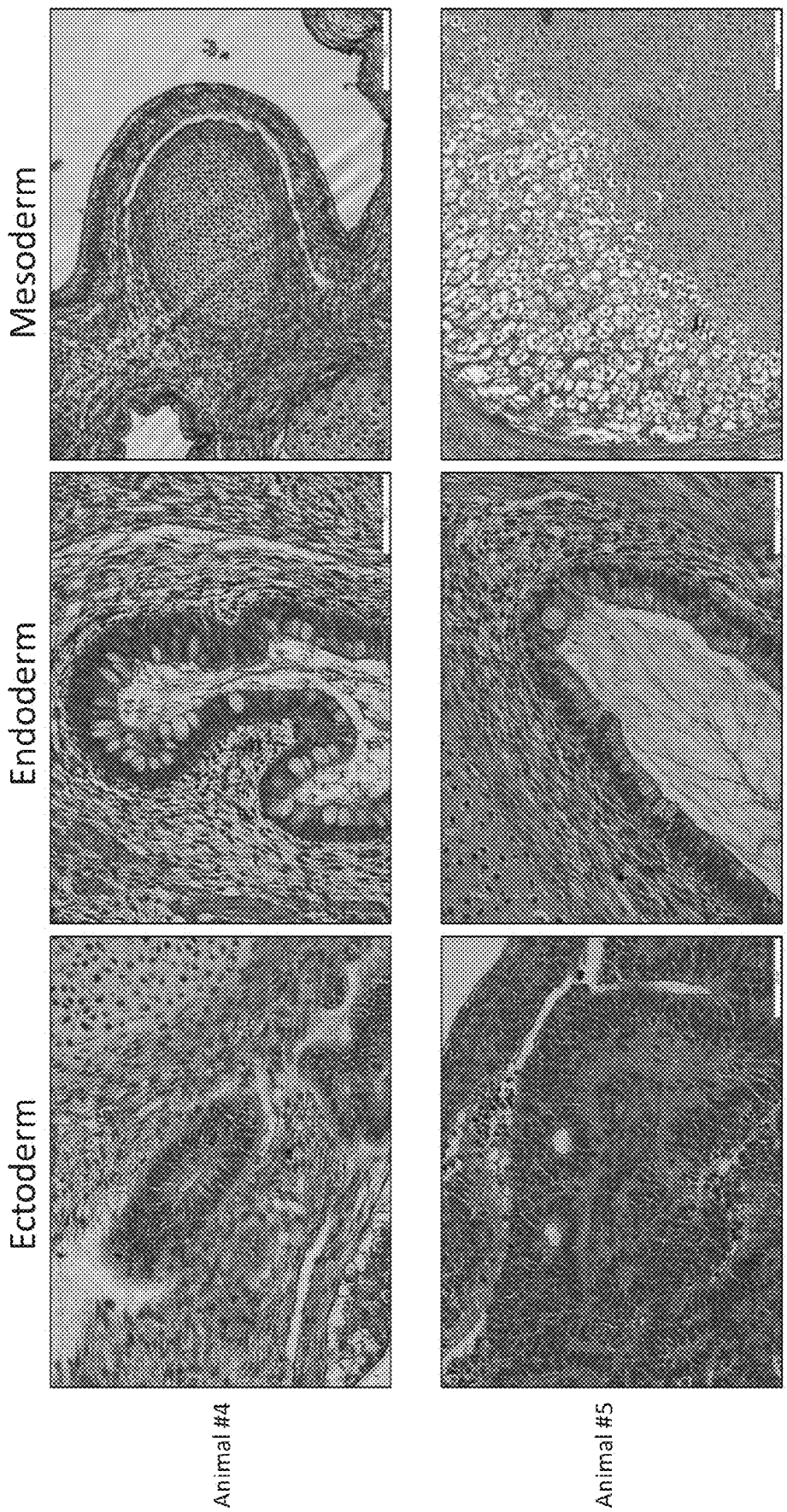

FIG. 9 are photomicrographs illustrating in-vivo differentiation within teratoma tumors—After transplanting #581 (46,XX) cells subcutaneously, the cells differentiated in teratomas into progeny representing the three germ layers. Hematoxylin-eosin stained histological sections showing neural rosettes (ectoderm), cartilage (mesoderm) and villi structures with columnar glandular epithelium (endoderm).

FIG. 10 illustrates karyotyping of cells of a patient (A.M) with a mosaic Karyotype (47,XXY/46,XY). A karyotype of cells with 46,XY and 47,XXY is demonstrated.

DESCRIPTION OF SPECIFIC EMBODIMENTS OF THE INVENTION

The present invention, in some embodiments thereof, relates to populations of autosomal-identical pluripotent stem cells having non-identical sex chromosomes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Over the past two decades a great deal how been learnt about how men and women respond differently to medications. This knowledge came after a concerted effort to increase the number of women in NIH-funded clinical research. Presently, just over half of NIH-funded clinical research participants are women. Unfortunately, experimental design in cell and animal research has not always followed suit. An over-reliance on male animals, and neglect of attention to the sex of cells, can lead to neglect of key sex differences that should be guiding clinical studies, and ultimately, clinical practice. However, currently there is no model to address sex and gender differences in humans.

The present inventors have now generated populations of induced pluripotent stem cells which are autosomal-identical, yet have non-identical sex chromosomes.

Such cells can serve as a human model for sex-dependent differences and allow examination of differences in all cell types and tissues in the human body. The cells may be used to study sex-dependent differences in basic research, drug development, regenerative medicine and disease modeling. Furthermore, the cells may be used to study the effect of X inactivation.

As illustrated herein under and in the examples section which follows, the present inventors have generated induced pluripotent stem cells (iPSCs) from blood cells of a subject having a sex chromosome mosaicism. Following karyotype analysis, the present inventors determined that all the iPSCs generated were autosomal-identical, yet were not identical to each other with respect to their sex chromosomes. As shown in Table 2, 7 different autosomal-identical iPSC populations were generated each with a different sex chromosome karyotype.

Thus, according to a first aspect of the present invention, there is provided a method of preparing iPSCs comprising dedifferentiating somatic cells of a subject having sex chromosome mosaicism under conditions that generate iPSCs, thereby preparing the iPSCs.

As used herein, the term "pluripotent cell" refers to a cell that has the potential to divide in vitro for a long period of time (e.g., greater than one year) and has the unique ability to differentiate into cells derived from all three embryonic germ layers—endoderm, mesoderm and ectoderm. Pluripotent cells have the potential to differentiate into the full range of daughter cells having distinctly different morphological, cytological or functional phenotypes unique to different specific tissues. By contrast, descendants of pluripotent cells are progressively restricted in their differentiation potential, with some cells eventually having only one fate.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin or blood cells) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc/LIN28 in a somatic stem cell.

According to one embodiment the method is effected by expressing in the cells at least one polypeptide belonging to the Oct family or the Sox family.

According to another embodiment, the method is effected by expressing in the cells at least two polypeptides—one belonging to the Oct family and one to the Sox family.

Examples of polypeptides belonging to the Oct family include, for example, Oct3/4 (NM_013633, mouse and NM_002701, human), Oct1A (NM_198934, mouse and NM_002697, human), Oct6 (NM_011141, mouse and NM_002699, human), and the like. Oct3/4 is a transcription factor belonging to the POU family, and is reported as a marker of undifferentiated cells (Okamoto et al., Cell 60:461-72, 1990). Oct3/4 is also reported to participate in the maintenance of pluripotency (Nichols et al., Cell 95:379-91, 1998).

Examples of polypeptides belonging to the Sox (SRY-box containing) family include, for example Sox1 (NM_009233, mouse and NM_005986, human), Sox3 (NM_009237, mouse and NM_005634, human), Sox7 (NM_011446, mouse and NM_031439, human), Sox15 (NM_009235, mouse and NM_006942, human), Sox17 (NM_011441, mouse and NM_022454, human) and Sox18 (NM_009236, mouse and NM_018419, human), and a preferred example includes Sox2 (NM_011443, mouse and NM_003106, human).

According to yet another embodiment, the method is effected by expressing in the cells four polypeptides—one belonging to the Oct family, one belonging to the Sox family, Nanog and LIN28.

According to yet another embodiment, the method is effected by expressing in the cells four polypeptides—one belonging to the Oct family, one belonging to the Sox family, KLF4 and LIN28.

Alternatively, the method is effected by expressing in the cells four polypeptides—one belonging to the Oct family, one belonging to the Sox family, KLF-4 and c-MYC.

Expressing the dedifferentiating factors described herein above in somatic cells may be performed by genetic manipulation—example using expression constructs. Various methods can be used to introduce the expression vectors of the present invention into the pancreatic beta cells. Such methods are generally described in, for instance: Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass.; and Gilboa, E. et al. (1986). Transfer and expression of cloned genes using retro-viral vectors. Biotechniques 4(6), 504-512; and include, for example, stable or transient transfection, lipofection, electroporation, and infection with recombinant viral vectors. In addition, see U.S. Pat. Nos. 5,464,764 and 5,487,992 for positive-negative selection methods.

Introduction of the expression constructs of the present invention into somatic cells by viral infection offers several advantages over other methods such as lipofection and electroporation offering higher efficiency of transformation and propagation. According to a particular embodiment, expressing the dedifferentiating factors described herein above in the somatic cells is performed by retroviral transduction.

Methods of inducing iPS cells without viral integration are also contemplated—see for example Stadtfeld et al., 2008, [Science 322, 945-949] and Okita et al., 2008, [Science 322, 949-953].

Alternatively, somatic cells may be transfected with mRNAs encoding the dedifferentiating factors [Givol et al., BBRC 394(2010): 189-193; Warren et al., Cell Stem Cell, Volume 7, Issue 5, 5 Nov. 2010, Pages 549-550] or by introduction of the proteins themselves (see for example Kim, D. et al. Cell Stem Cell doi:10.1016/j.stem.2009.05.005 (2009) and Zhou, H. Et al. Cell Stem Cell 4, 381-384, (2009).

Examples of culture media which may be used whilst inducing and culturing iPS cells include DMEM, DMEM/F12, or DME culture solutions (these culture solutions may further appropriately contain serum (e.g. 10-15%), LIF, antibiotics, L-glutamine, nonessential amino acids, beta-mercaptoethanol, or the like) or commercially available culture solutions e.g., a culture solution for culturing mouse ES cells (TX-WES culture solution, Thromb-X).

Currently practiced pluripotent stem cell culturing methods are mainly based on the use of feeder cell layers which secrete factors needed for stem cell proliferation, while at the same time, inhibit their differentiation. Feeder cell free systems may also been used in pluripotent cell culturing, such systems utilize matrices supplemented with serum, cytokines and growth factors as a replacement for the feeder cell layer.

Feeder-layer based cultures include the use of mouse feeder layers, human embryonic fibroblasts or adult fallopian epithelial cells as feeder cell layers and foreskin feeder layers.

As mentioned, the pluripotent stem cells may also be grown on feeder-free cultures e.g. on a solid surface such as an extracellular matrix (e.g., Matrigel® or laminin) in the presence of a culture medium. Unlike feeder-based cultures which require the simultaneous growth of feeder cells and stem cells and which may result in mixed cell populations, stem cells grown on feeder-free systems are easily separated from the surface. The culture medium used for growing the stem cells contains factors that effectively inhibit differentiation and promote their growth such as MEF-conditioned medium and bFGF.

Examples of culture media which may be used whilst inducing iPS cells include DMEM, DMEM/F12, or DME culture solutions (these culture solutions may further appropriately contain serum (e.g. 10-15%), LIF, antibiotics, L-glutamine, nonessential amino acids, beta-mercaptoethanol, or the like) or commercially available culture solutions e.g., a culture solution for culturing mouse ES cells (TX-WES culture solution, Thromb-X).

iPS cells can be selected depending on the shapes of the thus formed colonies. In some embodiments, a marker gene (e.g. an antibiotic resistance gene) is expressed in conjunction with one of the dedifferentiating factors, so that the thus established iPS cells can be selected. Furthermore, iPS cells can be selected through observation with a fluorescence microscope when a marker gene is a fluorescent protein gene, through addition of a luminescent substrate when a marker gene is a luminescent enzyme gene, or through addition of a chromogenic substrate when a marker gene is a chromogenic enzyme gene.

To generate isogenic cell lines, single cell colonies are selected and cultured in a medium which allows for maintenance of pluripotency, as described herein above.

Further analysis may be performed to assess the pluripotency characteristics of the iPS cells. The cells may be analyzed for different growth characteristics and embryonic stem cell like morphology. For example, cells may be differentiated in vitro by adding certain growth factors known to drive differentiation into specific cell types. Reprogrammed cells capable of forming only a few cell types of the body are multipotent, while reprogrammed cells capable of forming any cell type of the body are pluripotent.

Expression profiling of reprogrammed somatic cells to assess their pluripotency characteristics may also be conducted. Expression of individual genes associated with pluripotency may also be examined. Additionally, expression of embryonic stem cell surface markers may be analyzed. Detection and analysis of a variety of genes known in the art to be associated with pluripotent stem cells may include analysis of genes such as, but not limited to OCT4, NANOG, SALL4, SSEA-1, SSEA-3, SSEA-4, TRA-1-60, IRA-1-81, or a combination thereof. iPS cells may express any number of pluripotent cell markers, including: alkaline phosphatase (AP); ABCG2; stage specific embryonic antigen-1 (SSEA-1); SSEA-3; SSEA-4; TRA-1-60; 'IRA-1-81; Tra-2-49/6E; ERas/ECAT5, E-cadherin; .beta.-tubulin III; .alpha.-smooth muscle actin (.alpha.-SMA); fibroblast growth factor 4 (FGF4), Cripto, Dax1; zinc finger protein 296 (Zfp296); N-acetyltransferase-1 (Nath; ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthll7; Sall4; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tell); DPPA3/Stella; DPPA4; as well as other general markers for Pluripotency, for example any genes used during induction to reprogram the cell. IPS cells can also be characterized by the down-regulation of markers characteristic of the differentiated cell from which the iPS cell is induced.

In some embodiments, the sex of the iPSCs (e.g. of the single cell colonies) is analysed. This may be effected by various methods that are known in the art including but not limited to FISH, genomic RT-PCR (copy number variation assay), southern blot and karyotype. In all methods the sex chromosome complement is analyzed. Copy number variation assay may also be used to determine the copy number of X and Y chromosomes.

In other embodiments the karyotype of the iPSCs (e.g. of the single cell colonies) is analysed, in order to verify cytological euploidity, wherein all chromosomes are present and not detectably altered during culturing. Cultured stem cells can be karyotyped using a standard Giemsa staining and compared to published karyotypes of the corresponding species.

Exemplary methods for analyzing the chromosomal composition of the cells include chromosomal and DNA staining methods (e.g. FISH analysis, PRINS analysis, High-resolution multicolor banding (MCB) on interphase chromosomes and quantitative FISH (Q-FISH).

In an exemplary embodiment, iPSCs are pretreated with 0.02 µg/ml colecemid for about 2 to about 3 hours, incubated with about 0.06 to about 0.075M KCl for about 20 minutes, and then fixed with Carnoy's fixative. Afterwards, for multicolor FISH analysis, cells are hybridized with multicolor FISH probes, e.g., those in the Star*FISH™. Human Multicolour FISH (M-FISH) Kit from Cambio, Ltd (Cambridge, UK).

One of the characteristics of stem cells is their ability to proliferate continuously without undergoing senescence. Accordingly, iPSCs may be assessed for their ability to be passaged continuously in vitro. In some cases, the iPSCs are assayed for their ability to be passaged for at least about 30 to at least about 100 times in vitro, e.g., about 33, 35, 40, 45, 51, 56, 60, 68, 75, 80, 90, 93, 100, or any other number of passages from at least about 30 to at least about 100 passages.

In another evaluation, iPSCs are assayed for their ability to proliferate for a period of about 30 days to about 500 days from initiation of forced expression of IFs in parental cells, e.g., 40 days, 50 days, 60 days, 70 days, 80 days, 100 days, 150 days, 180 days, 200 days, 250 days, 300 days, 400 days, 450 days or any other period from about 30 days to about 500 days from initiation of forced expression of IFs in the parental cells. In some embodiments, long-term self-renewal of iPSCs is determined when the cells are passaged in a defined medium (e.g., mTeSR1 medium) and in the absence of feeder cells, e.g., mTeSR1 medium as described herein. In other embodiments, cells are passaged in MC-ES medium.

It is generally believed that pluripotent stem cells have the ability to form a teratoma, comprising ectodermal, mesodermal, and endodermal tissues, when injected into an immunocompromised animal. Induced cells or induced pluripotent stem cells (iPS) or ES cell-like pluripotent stem cells may refer to cells having an in vitro long-term self-renewal ability and the pluripotency of differentiating into three germ layers, and the pluripotent stem cells may form a teratoma when transplanted into a test animal such as mouse.

The iPSCs may be assessed for pluripotency in a teratoma formation assay in an immunocompromised animal model. The immunocompromised animal may be a rodent that is administered an immunosuppressive agent, e.g., cyclosporin or FK-506. For example, the immunocompromised animal model may be a SCID mouse. About $0.5 \times 10^6$ to about $2.0 \times 10^6$ e.g., $0.6 \times 10^6$, $0.8 \times 10^6$, $1.0 \times 10^6$, $1.2 \times 10^6$, $1.5 \times 10^6$, $1.7 \times 10^6$, or other number of iPSCs from about $0.5 \times 10^6$ to about $2.0 \times 10^6$ iPSCs/mouse may be injected into the medulla of a testis of a 7- to 8-week-old immunocompromised animal. After about 6 to about 8 weeks, the teratomas are excised after perfusing the animal with PBS followed by 10% buffered formalin. The excised teratomas are then subjected to immunohistological analysis. One method of distinguishing human teratoma tissue from host (e.g., rodent) tissue includes immunostaining for the human-specific nuclear marker HuNu. Immunohistological analysis includes determining the presence of ectodermal (e.g., neuroectodermal), mesodermal, and endodermal tissues. Protein markers for ectodermal tissue include, but are not limited to, nestin, GFAP, and integrin .beta.1. Protein markers for mesodermal tissue include, but are not limited to, collagen II, Brachyury, and osteocalcin. Protein markers for endodermal tissue include, but are not limited to, α-fetoprotein (αFP) and HNF3beta.

In some embodiments, global gene expression analysis is performed on putative iPS cell colonies. Such global gene expression analysis may include a comparison of gene expression profiles from a putative iPS cell colony with those of one or more cell types, including but not limited to, (i) parental cells, i.e., one or more cells from which the putative iPS cell colony was induced; (ii) a human ES cell line; or (iii) an established iPS cell line. As known in the art, gene expression data for human ES cell lines are available through public sources, e.g., on the world wide web in the NCBI "Gene Expression Omnibus" database. See, e.g., Barrett et al (2007), Nuc Acids Res, D760-D765. Thus, in some embodiments, comparison of gene expression profiles from a putative iPS colony to those of an ES cell line entails comparison experimentally obtained data from a putative iPS cell colony with gene expression data available through public databases. Examples of human ES cell lines for which gene expression data are publicly available include, but are not limited to, hE14 (GEO data set accession numbers GSM151739 and GSM151741), Sheff4 (GEO Accession Nos. GSM194307, GSM194308, and GSM193409), h_ES 01 (GEO Accession No. GSM194390), h_ES H9 (GEO Accession No. GSM194392), and h_ES BG03 (GEO Accession No. GSM194391).

It is also possible to accomplish global gene expression by analyzing the total RNA isolated from one or more iPS cell lines by a nucleic acid microarray hybridization assay. Examples of suitable microarray platforms for global gene expression analysis include, but are not limited to, the Human Genome U133 plus 2.0 microarray (Affymetrix) and the Whole Human Genome Oligo Micoarray (Agilent). A number of analytical methods for comparison of gene expression profiles are known as described in, e.g., Suarez-Farinas et al (2007), Methods Mol Biol, 377:139-152, Hardin et al (2007), BMC Bioinformatics, 8:220, Troyanskaya et al (2002), Bioinformatics, 18(11):1454-1461, and Knudsen (2002), A Biologist's Guide to Analysis of DNA Microarray Data, John Wiley & Sons. In some embodiments, gene expression data from cells produced by the methods described herein are compared to those obtained from other cell types including, but not limited to, human ES cell lines, parental cells, and multipotent stem cell lines. Suitable statistical analytical metrics and methods include, but are not limited to, the Pearson Correlation, Euclidean Distance, Hierarchical Clustering (See, e.g., Eisen et al (1998), Proc Natl Acad Sci USA, 95(25): 14863-14868), and Self Organizing Maps (See, e.g., Tamayo et al (1999), Proc Natl Acad Sci USA, 96(6):2907-2912.

As mentioned the somatic cells from which the iPSCs are generated are derived from a subject having sex chromosome mosaicism.

According to one embodiment, the somatic cells are derived from a subject having Turner syndrome.

According to another embodiment, the somatic cells are derived from a subject having Kleinefelter Syndrome.

At least a portion of the somatic cells which are used to generate the iPSC populations have a 46XX karyotype and another portion of the somatic cells which are used to generate the iPSC populations have a 46XY or 47XXY karyotype.

In another embodiment, a portion of the somatic cells which are used for generating the iPSC populations have a 46XX karyotype, another portion of the somatic cells which are used have a 46XY and another portion of the somatic cells which are used have a 47XXY karyotype.

Other additional karyotypes of the somatic cells contemplated for the present invention include 49,XXXXY and 45,X0.

In some embodiments, the iPS cells are further modified so as to deactivate at least one of the sex chromosomes. For example, when an iPSC has a 47,XXY karyotype, the present inventors contemplate knocking out or deactivating a gene on the Y chromosome such that the cells essentially become 46,XX karyotype.

Downregulation of a Y specific gene (e.g. SRY gene, DAZ1 gene, AZF1 gene and/or UTY gene) can be achieved by inactivating the gene via introducing targeted mutations involving loss-of function alterations (e.g. point mutations, deletions and insertions) in the gene structure.

The downregulating may be effected prior to the dedifferentiation stage or following the dedifferentiation stage.

As used herein, the phrase "loss-of-function alterations" refers to any mutation in the DNA sequence of a gene (e.g., SRY) which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frameshift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

Methods of introducing nucleic acid alterations to a gene of interest are well known in the art [see for example Menke D. Genesis (2013) 51: -618; Capecchi, Science (1989) 244:1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDS) and nonhomologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—

Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021, 867; 8,119,381; 8,124,369; 8,129,134; 8,133,697; 8,143, 015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—

Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, Calif.).

CRISPR-Cas System—

Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/ protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH—, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT).

The iPSC lines of the present invention may be comprised in an article of manufacture, as detailed herein below.

Thus, according to another aspect of the present invention there is provided an article of manufacture comprising at least two populations of autosomal-identical induced pluripotent stem cells (iPSCs), wherein the complement of sex chromosomes of the first population of the at least two populations is non-identical to the complement of sex chromosomes of the second population of the at least two populations.

The two populations of autosomal identical induced pluripotent stem cells are comprised in separate containers in the article of manufacture. In one embodiment, the two populations are stored in a bank.

The cell bank of this aspect of the present invention is a physical collection of iPS cell lines. Such banks preferably contain more than one sample (i.e., aliquot) of each iPS cell line. The bank may also contain one or more samples of the human feeder cells and/or serum used to expand the iPSC populations. The bank may comprise cell lines derived from a single donor or may comprise cell lines derived from multiple donors.

In one embodiment, the article of manufacture (e.g. cell bank) comprises a first population of iPSCs has a 46,XX karyotype and a second population has a 46,XY karyotype, both derived from the same subject (i.e. autosomal identical).

The article of manufacture (e.g. cell bank) may optionally include other autosomal identical iPSC populations include those having karyotype selected from the group consisting of 45X0, 93XXXXY and 47XXY.

The cell bank may also comprise cells differentiated from the iPSC lines, as further described herein below.

The iPS cell populations are stored under appropriate conditions (typically by freezing) to keep the stem cells alive and functioning. According to one embodiment, the iPSC populations are stored as cryopreserved populations. Other preservation methods are described in U.S. Pat. Nos. 5,656,498, 5,004,681, 5,192,553, 5,955,257, and 6,461,645. Methods for banking stem cells are described, for example, in U.S. Patent Application Publication No. 2003/0215942.

According to one embodiment, iPSCs stored in the bank are characterized according to at least one predetermined characteristic (e.g. karyotype, differentiation potential, donor information).

Other predetermined characteristics include, but are not limited to morphological characteristics, differentiation profile, blood type of donor, major histocompatibility complex, disease state of donor, or genotypic information (e.g. single nucleated polymorphisms, 'SNPs' of a specific nucleic acid sequence associated with a gene, or genomic or mitochondrial DNA).

Cataloguing may constitute creating a centralized record of the characteristics obtained for each cell population, such as, but not limited to, an assembled written record or a computer database with information inputted therein. The cell bank facilitates the selection from a plurality of samples of a specific iPSC line suitable for a researcher's or clinician's needs.

According to one embodiment, the cell bank described herein is maintained by a stem cell database computer unit. Each computer unit comprises at least one processing module, respectively, for processing information. The computer unit may be communicatingly connected to a display. Information directed to the stem cell populations may be stored on a database computer which is conveyed to users via a network connection. Such a system provides the customer the ability to evaluate the stem cell populations to determine which are suitable for their ongoing research and use and may also serve to facilitate the transaction of purchasing stem cells and proper shipment.

The iPSCs of the present invention have a myriad of uses. In one embodiment, the iPSCs are useful as a tool for drug screening.

Thus, according to another aspect of the present invention there is provided a method of analyzing the effect of an agent on cells:

(a) exposing a first population of iPS cells to the agent and determining an effect;

(b) exposing a second population of iPS cells to the agent and determining an effect; and (c) comparing the effect of step (a) with the effect of step (b), wherein the first and the second population of iPS cells are autosomal-identical iPSCs, wherein the complement of sex chromosomes of the first population of iPS cells is non-identical to the complement of sex chromosomes of the second population of iPS cells.

In one embodiment, the first population has a 46XX karyotype and the second population has a 46XY karyotype. According to this embodiment, the method may be used to compare the effect of an agent on a female cell and a male cell.

As used herein, the term "agent" refers to a test composition comprising a biological agent or a chemical agent or a condition.

When the agent is a test composition, preferably the agent is contacted physically with the cells.

Examples of biological agents that may be tested according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides), carbohydrates, hormones, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

According to a particular embodiment, the agent is a pharmaceutical.

According to a preferred embodiment of this aspect of the present invention the agents are differentiation agents including, but not limited to Examples of beta cell differentiation promoting agents include but are not limited to Activin A, Atrial Natriuretic Peptide, Betacellulin, Bone Morphogenic Protein (BMP-2), Bone Morphogenic Protein (BMP-4), C natriuretic peptide (CNP), Caerulein, Calcitonin Gene Related Peptide (CGRP-ax), Cholecystokinin (CCK8-amide), Cholecystokinin octapeptide (CCK8-sulfated), Cholera Toxin B Subunit, Corticosterone (Reichstein's substance H), Dexamethasone, DIF-1, Differanisole A, Dimethylsulfoxide (DMSO), EGF, Endothelin 1, Exendin 4, FGF acidic, FGF2, FGF7, FGFb, Gastrin I, Gastrin Releasing Peptide (GRP), Glucagon-Like Peptide 1 (GLP-1), Glucose, Growth Hormone, Hepatocyte Growth Factor (HGF), IGF-1, IGF-2, Insulin, KGF, Lactogen, Laminin, Leu-Enkephalin, Leukemia Inhibitory Factor (LIF), Met-Enkephalin, n Butyric Acid, Nerve Growth Factor (.beta.-NGF), Nicotinamide, n-n-dimethylformamide (DMF), Parathyroid Hormone Related Peptide (Pth II RP), PDGF AA+PDGF BB MIX, PIGF (Placental GF), Progesterone, Prolactin, Putrescine Dihydrochloride Gamma-Irradiated Cell Culture, REG1, Retinoic Acid, Selenium, Selenious Acid, Sonic Hedgehog, Soybean Trypsin Inhibitor, Substance P, Superoxide Dismutase (SOD), TGF-.alpha., TGF-.beta. sRII, TGF-.beta.1, transferrin, Triiodothyronine (T3), Trolox, Vasoactive Intestinal Peptide (VIP), VEGF, Vitamin A and Vitamin E.

Examples of conditions that may be tested on the iPSCs according to the method of the present invention include, but are not limited to radiation exposure (such as, gamma radiation, UV radiation, X-radiation).

In one embodiment the cells are analyzed to rule out/rule in toxic effects of the agent.

In another embodiment, the cells are analyzed for an effect on differentiation of the cells.

In other aspects of the present invention, the methods described herein further include inducing differentiation of the autosomal-identical cell lines of the present invention. Differentiation of cells may be accomplished by exposing cells to characterized factors which are known to produce a specific lineage outcome in the cells so exposed, so as to target their differentiation to that of a specific, desired lineage and/or cell type of interest. Alternatively, and/or additionally, differentiation may be accomplished by genetically modifying the cells to express a particular factor. Cells which are terminally differentiated display phenotypic characteristics of specialization and often lose the capacity to undergo indefinite culturing, exhibiting slowed proliferation.

The iPSCs as described herein may be differentiated into various cell types including any cell type of interest including endodermal (giving rise to cells of the endoderm, which gives rise to inner tissues and organs such as the alimentary canal, gut, digestive glands, respiratory system, and intestines/bladder), ectodermal (giving rise to cells of the ectoderm, which gives rise to the nervous system, skin, and other outermost specialized tissues and organs), mesodermal (giving rise to cells of the mesoderm; mesoderm is the middle germ layer of an embryo coming from the inner cell mass of the blastocyst; it gives rise to bone, muscle, connective tissues, including the dermis, the blood vascular system, the urogenital system except the bladder, and contributes to some glands), neuroectodermal (giving rise to any cells of the neuroectoderm, which gives rise to neurons, supporting cells, and ependyma of the central nervous system and the neural crest cells that form peripheral ganglia and a wide variety of other tissues), neural (giving rise to any cells of the nervous system peripheral and central; autonomic and somatic, including all neurons, support cells/glia, etc). In some embodiments, the cell line is differentiated into a population of cells, for example, a cobblestone-like cell line (e.g. retinal pigment epithelial cell population), a cardiomyocytic cell population, an epithelial cell population such as a keratin-containing or gut-like epithelial cell population, a gastrointestinal cell population, a respiratory cell population, a hepatic cell population, a pancreatic cell population, an endocrinic cell population, an epidermal cell population, a myogenic cell population, a cartilage cell population, a mucosal cell population, a skeletal cell population, a cartilage cell population, a nephritic cell population, a lymphatic cell population, a splenic cell population, or the precursors of any of the preceding.

In some embodiments, the cell population derived from the iPSCs is a multipotent cell population. In some embodiments, the cell population derived from the iPSCs is a monopotent cell population. In some embodiments, the cell population derived from the iPSCs is a terminally differentiated cell population. In some embodiments, the cell population derived from the iPSCs is capable of undergoing passage in culture without observed replicative crisis, up to and including days, weeks, months and years of passage in cell culture. In some embodiments, the cell population derived from the iPSCs is incapable of undergoing passage in culture without observed replicative crisis. In each case, the ordinarily skilled artisan can readily assess the viability and lineage potency of the derived cell population using methods known in the art.

There are numerous methods of differentiating the iPSCs into a more specialized cell type. Methods of differentiating iPSCs may be similar to those used to differentiate other stem cells, particularly ES cells, MSCs, MAPCs, MIAMI, hematopoietic stem cells (HSCs). In some cases, the differentiation occurs ex vivo; in some cases the differentiation occurs in vivo.

Thus, in some embodiments, the iPS cells may be differentiated into adult/tissue-specific stem cells, precursor, progenitor and differentiated cells.

Any known method of generating neural stem cells from ES cells may be used to generate neural stem cells from iPSCs, See, e.g., Reubinoff et al. (2001) Nat Biotechnol. 19(12):1134-40. For example, neural stem cells may be generated by culturing the iPSCs as floating aggregates in the presence of noggin, or other bone morphogenetic protein antagonist, see e.g., Itsykson et al. (2005) Mol Cell Neurosci. 30(1):24-36. In another example, neural stem cells may be generated by culturing the iPSCs in suspension to form aggregates in the presence of growth factors, e.g., FGF-2, Zhang et al. (2001), Nat. Biotech. (19) 1129-1133. In some cases, the aggregates are cultured in serum-free medium containing FGF-2. In another example, the iPSCs are co-cultured with a mouse stromal cell line, e.g., PA6 in the presence of serum-free medium comprising FGF-2. In yet another example, the iPSCs are directly transferred to serum-free medium containing FGF-2 to directly induce differentiation.

Neural stems derived from the iPSCs may be differentiated into neurons, oligodendrocytes, or astrocytes. Dopaminergic neurons play a central role in Parkinson's Disease and are thus of particular interest. In order to promote differentiation into dopaminergic neurons, iPSCs may be co-cultured with a PA6 mouse stromal cell line under serum-free conditions, see, e.g., Kawasaki et al. (2000) Neuron 28(1):31-40. Other methods have also been described, see, e.g., Pomp et al. (2005), Stem Cells 23(7): 923-30; U.S. Pat. No. 6,395,546 and Kriks et al, Nature, 2011, Volume 480, pages 547-551.

Oligodendrocytes may also be generated from the iPSCs. For example, oligodendrocytes may be generated by co-culturing iPSCs or neural stem cells with stromal cells, e.g., Lee et al. (2000) Nature Biotechnol 18:675-679. In another example, oligodendrocytes may be generated by culturing the iPSCs or neural stem cells in the presence of a fusion protein, in which the Interleukin (IL)-6 receptor, or derivative, is linked to the IL-6 cyotkine, or derivative thereof.

Astrocytes may also be produced from the iPSCs. Astrocytes may be generated by culturing iPSCs or neural stem cells in the presence of neurogenic medium with bFGF and EGF, see e.g., Brustle et al. (1999) Science 285:754-756.

Induced cells may be differentiated into pancreatic beta cells by methods known in the art, e.g., Lumelsky et al. (2001) Science 292:1389-1394; Assady et al., (2001) Diabetes 50:1691-1697; D'Amour et al (2006) Nat Biotechnol: 1392-1401' D'Amouret et al. (2005) Nat Biotechnol 23:1534-1541. The method may comprise culturing the iPSCs in serum-free medium supplemented with Activin A, followed by culturing in the presence of serum-free medium supplemented with all-trans retinoic acid, followed by culturing in the presence of serum-free medium supplemented with bFGF and nicotinamide, e.g., Jiang et al. (2007) Cell Res 4:333-444. In other examples, the method comprises culturing the iPSCs in the presence of serum-free medium, activin A, and Wnt protein from about 0.5 to about 6 days, e.g., about 0.5, 1, 2, 3, 4, 5, 6, days; followed by culturing in the presence of from about 0.1% to about 2%, e.g., 0.2%, FBS and activin A from about 1 to about 4 days, e.g., about 1, 2, 3, 4 days; followed by culturing in the presence of 2% FBS, FGF-10, and KAAD-cyclopamine (keto-N-aminoethylaminocaproyl dihydro cinnamoylcyclopamine and retinoic acid from about 1 to about 5 days, e.g., 1, 2, 3, 4, or 5 days; followed by culturing with 1% B27, gamma secretase inhibitor and extendin-4 from about 1 to about 4 days, e.g., 1, 2, 3, or 4 days; and finally culturing in the presence of 1% B27, extendin-4, IGF-1, and HGF for from about 1 to about 4 days, e.g., 1, 2, 3, or 4 days.

Hepatic cells or hepatic stem cells may be differentiated from the iPSCs. For example, culturing the iPSCs in the presence of sodium butyrate may generate hepatocytes, see e.g., Rambhatla et al. (2003) Cell Transplant 12:1-11. In another example, hepatocytes may be produced by culturing the iPSCs in serum-free medium in the presence of Activin A, followed by culturing the cells in fibroblast growth factor-4 and bone morphogenetic protein-2, e.g., Cal et al. (2007) Hepatology 45(5):1229-39. In an exemplary embodiment, the iPSCs are differentiated into hepatic cells or hepatic stem cells by culturing the iPSCs in the presence of Activin A from about 2 to about 6 days, e.g., about 2, about 3, about 4, about 5, or about 6 days, and then culturing the iPSCs in the presence of hepatocyte growth factor (HGF) for from about 5 days to about 10 days, e.g., about 5, about 6, about 7, about 8, about 9, or about 10 days. Other exemplary methods for differentiating the iPSCs to hepatic cells are disclosed in Duan et al., Stem Cells, 2010, 28:674-686 and Gomez-Lechon et al., Arch Toxicol, 2016, 90:2049-2061, the contents of which are disclosed herein in their entirety.

The method may also comprise differentiating iPSCs into cardiac muscle cells. In an exemplary embodiment, the method comprises culturing the iPSCs in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

In other examples, cardiomyocytes may be generated by culturing the iPSCs may in the presence of LIF, or by subjecting them to other methods in the art to generate cardiomyocytes from ES cells, e.g., Bader et al. (2000) Circ Res 86:787-794, Kehat et al. (2001) J Clin Invest 108:407-414; Mummery et al. (2003) Circulation 107:2733-2740.

Examples of methods to generate other cell-types from iPSCs include: (1) culturing iPSCs in the presence of retinoic acid, leukemia inhibitory factor (LIF), thyroid hormone (T3), and insulin in order to generate adipoctyes, e.g., Dani et al. (1997) J. Cell Sci 110:1279-1285; (2) culturing iPSCs in the presence of BMP-2 or BMP-4 to generate chondrocytes, e.g., Kramer et al. (2000) Mech Dev 92:193-205; (3) culturing the iPSCs under conditions to generate smooth muscle, e.g., Yamashita et al. (2000) Nature 408: 92-96; (4) culturing the iPSCs in the presence of beta-mercaptoethanol to generate keratinocytes, e.g., Bagutti et al. (1996) Dev Biol 179: 184-196; Green et al. (2003) Proc Natl Acad Sci USA 100: 15625-15630; (5) culturing the iPSCs in the presence of Interleukin-3 (IL-3) and macrophage colony stimulating factor to generate macrophages, e.g., Lieschke and Dunn (1995) Exp Hemat 23:328-334; (6) culturing the iPSCs in the presence of IL-3 and stem cell factor to generate mast cells, e.g., Tsai et al. (2000) Proc Natl Acad Sci USA 97:9186-9190; (7) culturing the iPSCs in the presence of dexamethasone and stromal cell layer, steel factor to generate melanocytes, e.g., Yamane et al. (1999) Dev Dyn 216:450-458; (8) co-culturing the iPSCs with fetal mouse osteoblasts in the presence of dexamethasone, retinoic acid, ascorbic acid, beta-glycerophosphate to generate osteoblasts, e.g., Buttery et al. (2001) Tissue Eng 7:89-99; (9) culturing the iPSCs in the presence of osteogenic factors to generate osteoblasts, e.g., Sottile et al. (2003) Cloning Stem Cells 5:149-155; (10) overexpressing insulin-like growth factor-2 in the iPSCs and culturing the cells in the presence of dimethyl sulfoxide to generate skeletal muscle cells, e.g., Prelle et al. (2000) Biochem Biophys Res Commun 277:631-638; (11) subjecting the iPSCs to conditions for generating white blood cells, e.g., Rathjen et al. (1998) Reprod Fertil Dev 10:31-47; or (12) culturing the iPSCs in the presence of BMP4 and one or more: SCF, FLT3, IL-3, IL-6, and GCSF to generate hematopoietic progenitor cells, e.g., Chadwick et al. (2003) Blood 102:906-915. Another exemplary protocol for differentiating the cells of the present invention into cardiomyocytes is disclosed in Shinnawi et al., Stem Cell Reports, Vol. 5, 582-596, Oct. 13, 2015, the contents of which is incorporated herein by reference.

Thus, according to another aspect of the present invention there is provided an article of manufacture (e.g. cell bank) comprising at least two populations of cells being of an identical cell type (e.g. somatic or germ cell), the at least two populations being autosomal-identical and having been differentiated ex vivo from iPSCs derived from a subject having sex chromosome mosaicism, wherein the complement of sex chromosomes of the first population of the at least two populations is non-identical to the complement of sex chromosomes of the second population of the at least two populations.

In one embodiment, the cell populations are genetically modified to express at least one dedifferentiating factor selected from the group consisting of KLF4, c-MYC, OCT4, SOX2, Nanog, and LIN28.

Examples of somatic cell types retinal pigment epithelial cells, cardiomyocytes, epithelial cells such as keratin-containing cells, hepatocytes, pancreatic cells (e.g. pancreatic beta cells), muscle cells, blood cells, fat cells, bone cells, chondrocytes, neurons, astrocytes and oligodendrocytes.

According to a particular embodiment, the somatic cells are selected from the group consisting of neuronal cells, cardiac cells, pancreatic cells, hepatic cells and skin cells. The article of manufacture/cell bank of this aspect of the present invention may further comprise the populations of iPSCs from which the somatic/germ cells were derived.

The somatic/germ cells of this aspect of the present invention may also be used for drug screening and disease modeling.

Thus according to another aspect of the present invention there is provided a method of analyzing the effect of an agent on cells:

(a) exposing a first population of cells to the agent and determining an effect;

(b) exposing a second population of cells being of the same type as the first population of somatic cells to the agent, and determining an effect; and (c) comparing the effect of step (a) with the effect of step (b), wherein the first and the second population of somatic cells are autosomal-identical, wherein the complement of sex chromosomes of the first population of somatic cells is non-identical to the complement of sex chromosomes of the second population of somatic cells.

Examples of agents that may be analyzed are described herein above with respect to the iPSC cells.

Exemplary effects that may be analyzed are described herein above with respect to the iPSC cells.

It is expected that during the life of a patent maturing from this application many relevant differentiation and dedifferentiating agents will be developed and the scope of these two terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods
Cell Culture:
EBV-immortalized B-cells were cultured in RPMI medium (RPMI supplemented with 15% Fetal Calf Serum, 0.2 mM L-glutamine, 50 U/ml penicillin and 50 µg/ml streptomycin) at 37° C., 5% $CO_2$. During reprogramming, reprogramming medium was used. Reprograming medium contained DMEM/F12 supplemented with 1% NEAA, 1% Glutamine, 1% N2, 2% B27, 0.5% antibiotic antimycotic (Gibco #15240-062), 0.1 µM Beta-mercaptoethanol, 100 ng/ml bFGF (peprotech), 1:1000 (~1000 units) hLIF (Millipore #LIF1010), 0.5 µM PD0325901 (Cayman Chemicals, #13034), 3 µM CHIR99021 (Tocris, #4423), 10 µM HA-100 (Santa Cruz Biotech, #203072), and 0.5 µM A-83-01 (Tocris, #2939). iPS cells were plated on GF-reduced matrigel (Corning, N.Y., USA) in mTesr1 medium (STEMCELL technologies, Vancouver, Canada) and expanded mechanically.

Fluorescence In Situ Hybridization (FISH) and Karyotype:
FISH analysis included the following probes: CEP X(DXZ1)/Y(DYZ3) and CEP 18(DXZ1). Chromosomes X, Y and 18 were directly labeled with green, red and blue fluorescent haptens respectively (CEP® Spectrum aqua; Vysis Naperville, Ill., USA). The hybridization targets for the 18 and X probes were α-satellite repeat clusters in the centromeric region of these chromosomes. The Y probe was specific for satellite III DNA at the heterochromatic region of the long arm of Y chromosome. The FISH protocol followed the manufacturer's guidelines with slight modifications. The slide was placed on a programmable slide warmer in a dark and moist chamber (HYBrite hybridization system; Vysis) for denaturation at 75° C. for 5 min followed by hybridization at 37° C. for 30 min. Post-hybridization washings was done according to the manufacturer's rapid wash procedure. The slides were then counterstained with 49,6-diamidino-2-phenylindole (DAPI) in anti-fade solution (Cytocell, Cambridge, UK). Fluorescence microscopy was performed with an automated Olympus BX61 microscope (Olympus, Tokyo, Japan).

For karyotype analysis, cells were incubated for 30-40 minutes with 100 ng/ml Colcemid (Biological Industries, Beit Haemek, Israel) and then dissociated with trypsin (Gibco). Incubation in hypotonic solution, fixation and G-banding technique were as previously described (Benn and Perle, 1992). Full karyotype analysis were performed on 10 metaphases spreads, and chromosome counting on an additional 10 spreads.

Reprogramming EBV-Immortalized B Cells to Induced Pluripotent Stem Cells (iPS Cells).

Reprogramming was performed according to Barrett et al. [24]. Briefly, $10^6$ cells were nucleofected using B-cell Nucleofector Kit (VPA-1001, Lonza) with 4 plasmids containing the following genes: SOX2, OCT4, KLF4, LIN28, L-MYC, SV40LT, shP53 (Addgene). The cells were plated on matrigel with RPMI medium for 3 days. Reprogramming media was added gradually in the next 3 days, 1 ml each day. Reprogramming media was changed every other day for the next 15 days, and then mTesr1 media was used for the growth of iPS cells.

iPS Cell Characterization

Alkaline Phosphatase Activity Detection:

Vector Red Alkaline Phosphatase substrate kit I (Vector Laboratories Inc., Burlingame, Calif., US), Alkaline Phosphatase Staining Kit II (Stemgent, Cambridge, Mass., USA), or AP Substrate Kit (Sigma) were used for detection of alkaline phosphatase activity within intact colonies on feeders according to the manufacturer's instructions.

Immunostaining:

hESCs colonies that were cultured on feeder layer for 4-6 days were fixed with 4% paraformaldehyde for 20 min at RT. For immunostaining of intracellular markers, cell membranes were permeabilized with 0.2% Triton X100 (Sigma), 5% normal goat serum (Beit Haemek) in PBS for 20 min. The cells were incubated for 20-30 min at RT with the following primary antibodies: anti-human Oct-3/4 antibody (1:50; Santa Cruz Biotechnology Inc., USA), mouse monoclonal anti-human TRA-1-60 (1:50), TRA-1-81 (1:50) and SSEA-4 (1:50) antibodies (all from Chemicon International, Temecula, Calif., USA) followed by [fluorescein isothiocyanate (FITC)]-labeled goat anti-mouse immunoglobulin (1:50, Dako). Rat monoclonal anti-human SSEA-3 (1:50, Chemicon), followed by mouse anti-rat IgM conjugated to R-PE, (1:20; Southern Biotechnology Associates Birmingham, Al, USA) or Alexa Fluor-488 labeled goat anti-rat IgM (1:100, Invitrogen). Rabbit Polyclonal Anti KI-67 (1:100, Novo Castra Laboratories), followed by FITC-conjugated Polyclonal Swine Anti-Rabbit Immunoglobulins (1:10, Dako) was used. Mounting medium containing DAPI (Vector) was used for nuclei counterstaining and the specimens were visualized with a Nikon E600 fluorescent microscope.

FACS Analysis:

hESC colonies were dissociated with 0.05% EDTA solution followed by gentle trituration to a single-cell suspension. The hESCs were centrifuged and re-suspended in FACS buffer. The cells were incubated with anti-TRA-1-60 (1:100), anti-TRA-1-81 (1:100), anti SSEA-4 (1:200), anti SSEA-1 (1:300; all from Chemicon) and anti SSEA-3 (1:100, Millipore) for 30 min at 4° C. As control, hESCs were stained with respective isotype control antibodies (all from eBiosciences). Following washing, primary antibodies were detected by incubating with FITC-labeled goat anti-mouse Ig (1:100, Dako) and goat anti-rat Ig (1:100, Invitrogen) for 30 min at 4° C. Following washing, the cells were resuspended in FACS buffer supplemented with PI (1:500 of 1 mg/ml solution, Sigma). FACS analysis was performed using the FACSCalibur system (Becton Dickinson).

Analysis of Pluripotency In Vitro:

Colonies of undifferentiated hESCs were mechanically removed from the feeders and cultured in suspension as embryoid bodies (EBs) or neurospheres. For the development of EBs, the hESC free-floating clusters were cultured 3 weeks in DMEM supplemented with 15-20% FCS, 2 mM L-glutamine, 1% nonessential amino acids, 50 U/ml penicillin, 50 µg/ml streptomycin, 0.1 mM beta-mercaptoethanol (all from Invitrogen). Neurospheres were developed as previously described [56]. Briefly, the hESC clusters were cultured 3 weeks in DMEM/F12 (1:1) supplemented with B-27 (1:50), 2 mM L-Glutamine, 50 U/ml penicillin, 50 µg/ml streptomycin (all from Invitrogen), 20 ng/ml bFGF and 500 ng/ml rm-Noggin (both from Peprotech, London, UK).

After the 3 weeks of suspension culture, the EBs and the neurospheres were partially dissociated by mild trypsin digestion and plated on glass coverslips pretreated with 10 µg/ml poly-d-lysine (Sigma) and 4 µg/ml laminin (Sigma), and cultured for an additional 5-7 days in the respective culture media as above in the absence of noggin and bFGF. They were fixed with 4% paraformaldehyde and then stained with mouse monoclonal anti-beta-tubulin isotype III (1:2000; Sigma), mouse monoclonal anti-human desmin (1:50; Dako), or mouse monoclonal anti-human muscle actin (1:50; Dako), and mouse monoclonal anti-human sox-17 (1:50; R&D).

Polyclonal goat anti-mouse immunoglobulins conjugated to FITC (1:50, Dako) or to Cy3 (1:1000, Jackson Laboratories) were used to detect the primary antibodies. Mounting and visualization was performed as above.

Analysis of Pluripotency In Vivo:

Subject to an approval of the Institutional Ethical Committee for Care and Use of Animals, 4-5 week old NOD SCID mice (Harlan, Jerusalem, Israel) were subcutaneously inoculated utilizing a 25 G needle with 100-200 small clusters of approximately 500 cells of undifferentiated hESCs in each cluster, which had been mechanically removed from the feeders. The hESCs were injected with $1\times10^6$ irradiated cord fibroblasts cells, in a total volume of 60 ul, together with an equal volume of Matrigel (Basement membrane matrix, Becton Dickenson Biosciences). Maximum teratoma size permitted was 15 mm. 8-12 weeks later, the resulting tumors were removed, fixed in neutral buffered 4% formalin, embedded in paraffin, and examined histologically after hematoxylin and eosin staining.

Copy Number Variation (CNV) Assay:

Genomic DNA was extracted from iPSCs colonies using quick-gDNA MicroPrep (Zymo research, Irvine, Calif., USA). The gDNA was diluted to a final concentration of 5 ng/µL. TaqMan Copy Number Assays (Thermo Fisher Scientific, Waltham, Mass., USA) were used to evaluate the copy number of genomic DNA targets. Probes for SRY on Y chromosome and XIST, ARSH on X chromosomes were used (Hs01026408_cn, Hs04111313_cn, Hs00622494_cn respectively). The Applied Biosystems protocols that use a duplex TaqMan real-time quantitative polymerase chain reaction (qPCR) method were employed for every sample. Basically, each reaction (10 μL) contained 5 μL master mix, 2 μL gDNA, 0.5 μL TaqMan Copy Number Assay, 0.5 μL TaqMan Copy Number Reference Assay (RNAseP), and 2 μL nuclease free water. All reactions were run in triplicates with PCR cycling conditions as follows: 1 PCR cycle at 95° C. for 10 min, followed by 40 cycles at 95° C. for 15 sec and 60° C. for 1 min. Data was analyzed using CopyCaller v2.1 software (Applied Biosystems). Foreskin fibroblasts and XX unbilical cord cells were used as control samples. Genomic DNA for control samples was extracted using Wizard genomic DNA Purification Kit (Promega, Madison, Wis., USA).

STR Fingerprinting and Human Leukocyte Antigen (HLA) Testing:

iPSCs were cultured in a feeder-free culture system in order to eliminate contamination. STR analysis was performed as described above for feeders. For HLA profiling, the DNA was extracted using the MagNA Pure LC machine (Roche Applies Sciences, Indianapolis, Ind., USA). For HLA profiling, the DNA was extracted using the MagNA Pure LC machine (Roche Applies Sciences, Indianapolis, Ind., USA). HLA-A, B, DRB1, DQB1 loci at low resolution were typed using the Lipa HLA kit (Murex Immunogenetics, Ghent, Belgium). High resolution typing of the HLA-DRB1 and DQB1 alleles used the PCR-Sequence Specific Primers method (PCR-SSP, Olerup kit, Olerup, Stockholm, Sweden), according to the manufacturer's instructions. The HLA and STR analyses were done in the Hadassah Tissue Typing Unit.

Results

Characterization of GM17906 EBV-Immortalized B Cells

GM17906 is an EBV-immortalized B cell line of a clinically affected patient with mosaic Kleinefelter Syndrome. According to the published karyotype, GM17906 contains: 47,XXY[39]/46,XX[2]/46,XY[7]/46,XX,dic(Y; 18) (Ypter>Yq12::18q23>18pter) [2]

In order to verify the karyotype, FISH analysis for X and Y centromeres was performed on GM17906 cell line. Out of 137 cells, 71.5% were 47,XXY, 25% were 46,XY and 3.5% were 46,XX—see Table 1, herein below and FIGS. 1A-C.

TABLE 1

| Karyotype | No. of cells | % of cells |
|---|---|---|
| 47 XXY | 98 | 71.5 |
| 46XY | 34 | 25 |
| 46XX | 5 | 3.5 |

Another full karyotype analysis for 20 cells was performed in order to corroborate these results, showing mosaic karyotype of 47,XXY[8]/46,XY[7]/46,XX[1]/4 other cells with dicentric chromosomes and translocations.

Thus, the cell line has 47,XXY cells, 46,XY cells and 46,XX cells with a normal karyotype and possibly identical autosomal chromosomes.

Reprogramming of EBV-Immortalized B Cells to iPS Cells:

EBV-immortalized B cells were cultured as floating clumps. The cells were reprogrammed as single cells via nucleofection of four plasmids according to Barrett et al. [24]. Transfected cells were plated sparsely to enable cloning in feeder-free condition on matrigel-coated plates. Adherent colonies appeared on the plate, approximately 7 days following transfection. Approximately 2 weeks later, each colony was passaged to a new center well dish and expanded mechanically.

For screening of XX and XY cells, genomic DNA was extracted for copy number variation assay on SRY (Y chromosome) and XIST, ARSH (Y chromosome). Out of 80 colonies, 29 were suspected as XY, 3 as XX and the rest were XXY. 7 colonies were sent to karyotype: 2 colonies were verified as 46,XY (#10, #59), and the other were 47,XXY (#36), 93,XXXXY (#16), 45,X0 (#63), 47,XXY/trans(1; 3) (#60), and one colony was mosaic of normal 46,XX euploid cells (43%), 47,XXY (19%), and 46,XY abnormal cells (38%) (#57). This last colony was sub-cloned and of 16 clones that were obtained and screened, 14 clones were XX. Three clones were sent for karyotyping and one was found to be euploid 46XX cell line.

Altogether, the present inventors isolated 45,X0, 46,XX, 46,XY, 47,XXY and 93,XXXXY autosomal-identical iPSC lines—see FIG. 2 and Table 2 herein below.

TABLE 2

| Identification number of clones | karyotype |
|---|---|
| 10 | 46, XY |
| 16 | 93,XXXXY |
| 36 | 47,XXY |
| 57 | 47,XXY/abnormal 46,XX/46,XX |
| 57 (sub-clone 11) | 46,XX |
| 59 | 46,XY |
| 60 | 47,XXY/(trans1:3) |
| 63 | 45,X0 |
| 21 | 47,XXY |
| 272 | 46,XX |
| 56 | 47,XXY |
| 581 | 46,XX | ipSC Line Characterization:

The colonies of all clones showed morphological characteristics typical to pluripotent stem cells. The colonies were flat with distinct borders, and were comprised of small tightly packed cells with high nuclear cytoplasmatic ratio and prominent nucleoli.

For further characterization, the cells were cultured on feeder cells in KO medium. The hiPSC colonies showed typical morphology and alkaline phosphatase activity and had no autosomal chromosome abnormalities (FIGS. 3 and 4A-D). The cells were also immunoreactive with anti OCT-4, TRA-1-60, TRA-1-81 and SSEA-4 antibodies pluripotent markers (FIG. 5).

The pluripotent potential of the hiPSC lines was demonstrated by their capability to differentiate into progeny representing the three embryonic germ layers in-vitro and in-vivo. Following 3-4 weeks of differentiation as embryoid bodies (EBs), clusters were dissociated and seeded on laminin coated slides for further differentiation. After 3 weeks, immunofluorescence staining showed cells expressing beta-tubulin III (neuronal marker, ectoderm) and human muscle actin (mesoderm) (FIG. 6).

When clusters of hiPSCs from the cell lines were inoculated subcutaneously into SCID mice, teratoma tumors developed and were analyzed histologically after 8-12 weeks. H&E sections showed neural rosettes (ectoderm), cartilage (mesoderm) and columnar glandular epithelium with goblet cells (endoderm)(FIGS. 7-10).

Generation of Cell Bank:

The cells were scraped using a rubber policemen and were frozen within 1 ml of 90% FCS and 10% DMSO, by a standard slow cooling procedure. The vials were stored in the vapor phase of liquid nitrogen tanks (−180° C.). Thirty vials of each cell line were frozen.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Vaccarino, V., et al., Sex-based differences in early mortality after myocardial infarction. National Registry of Myocardial Infarction 2 Participants. N Engl J Med, 1999. 341(4): p. 217-25.
2. Whitacre, C. C., Sex differences in autoimmune disease. Nat Immunol, 2001. 2(9): p. 777-80.
3. Loke, H., V. Harley, and J. Lee, Biological factors underlying sex differences in neurological disorders. Int J Biochem Cell Biol, 2015. 65: p. 139-50.
4. Schaafsma, S. M. and D. W. Pfaff, Etiologies underlying sex differences in Autism Spectrum Disorders. Front Neuroendocrinol, 2014. 35(3): p. 255-71.
5. Gobinath, A. R., R. Mahmoud, and L. A. Galea, Influence of sex and stress exposure across the lifespan on endophenotypes of depression: focus on behavior, glucocorticoids, and hippocampus. Front Neurosci, 2014. 8: p. 420.
6. Goldstein, J. M., et al., Sex differences in the genetic risk for schizophrenia: history of the evidence for sex-specific and sex-dependent effects. Am J Med Genet B Neuropsychiatr Genet, 2013. 162B(7): p. 698-710.
7. Pollitzer, E., Biology: Cell sex matters. Nature, 2013. 500(7460): p. 23-4.
8. Jagsi, R., et al., Under-representation of women in high-impact published clinical cancer research. Cancer, 2009. 115(14): p. 3293-301.
9. Greenspan, J. D., et al., Studying sex and gender differences in pain and analgesia: a consensus report. Pain, 2007. 132 Suppl 1: p. S26-45.
10. Deasy, B. M., et al., A role for cell sex in stem cell-mediated skeletal muscle regeneration: female cells have higher muscle regeneration efficiency. J Cell Biol, 2007. 177(1): p. 73-86.
11. Du, L., et al., Innate gender-based proclivity in response to cytotoxicity and programmed cell death pathway. J Biol Chem, 2004. 279(37): p. 38563-70.
12. Ronen, D. and N. Benvenisty, Sex-dependent gene expression in human pluripotent stem cells. Cell Rep, 2014. 8(4): p. 923-32.
13. Clayton, J. A. and F. S. Collins, Policy: NIH to balance sex in cell and animal studies. Nature, 2014. 509(7500): p. 282-3.
14. Chen, X., et al., The number of x chromosomes causes sex differences in adiposity in mice. PLoS Genet, 2012. 8(5): p. e1002709.
15. Cox, K. H., P. J. Bonthuis, and E. F. Rissman, Mouse model systems to study sex chromosome genes and behavior: relevance to humans. Front Neuroendocrinol, 2014. 35(4): p. 405-19.
16. Thomson, J. A., et al., Embryonic stem cell lines derived from human blastocysts. Science, 1998. 282(5391): p. 1145-7.
17. Reubinoff, B. E., et al., Embryonic stem cell lines from human blastocysts: somatic differentiation in vitro. Nat Biotechnol, 2000. 18(4): p. 399-404.
18. Takahashi, K., et al., Induction of pluripotent stem cells from adult human fibroblasts by defined factors. Cell, 2007. 131(5): p. 861-72.
19. Fruhmesser, A. and D. Kotzot, Chromosomal variants in klinefelter syndrome. Sex Dev, 2011. 5(3): p. 109-23.
20. Sokol, R. Z., It's not all about the testes: medical issues in Klinefelter patients. Fertil Steril, 2012. 98(2): p. 261-5.
21. Al-Awadi, S. A., et al., Klinefelter's syndrome, mosaic 46,XX/46,XY/47,XXY/48,XXXY/48,XXYY: a case report. Ann Genet, 1986. 29(2): p. 119-21.
22. Karimi, H., et al., A Rare Case of Klinefelter Syndrome Patient with Quintuple Mosaic Karyotype, Diagnosed by GTG-Banding and FISH. Int J Fertil Steril, 2014. 8(2): p. 221-4.
23. Zamora, L., et al., Report of 46,XX/46,XY/47,XXY/48, XXYY mosaicism in an adult phenotypic male. Am J Med Genet, 2002. 111(2): p. 215-7.
24. Barrett, R., et al., Reliable generation of induced pluripotent stem cells from human lymphoblastoid cell lines. Stem Cells Transl Med, 2014. 3(12): p. 1429-34.

What is claimed is:

1. A method of analyzing whether an agent has a sex-dependent, toxic effect on human induced pluripotent stem (iPS) cells comprising:
    (a) exposing a first population of human iPS cells to the agent and analyzing whether the agent has a toxic effect on said first population of human iPS cells;
    (b) exposing a second population of human iPS cells to the agent and analyzing whether the agent has a toxic effect on said second population of human iPS cells; wherein the autosome of said first population of iPS cells is identical to the autosome of said second population of iPS cells, wherein the complement of sex chromosomes of the first population of iPS cells is non-identical to the complement of sex chromosomes of the second population of iPS cells; and
    (c) comparing the effect of the agent on said first population of human iPS cells with the effect of the agent on said second population of human iPS cells, wherein a difference between the toxic effect on the first population of human iPS cells and the toxic effect on the second population of human iPS cells is indicative that the agent has a sex-dependent toxic effect on human iPS cells.

2. The method of claim 1, wherein said first population has a 46XY karyotype and said second population has a 46XX karyotype.

3. The method of claim 1, wherein said first population has a 46XY karyotype and said second population has a 47XXY karyotype with deletion in a Y specific gene.

4. The method of claim 1, wherein said agent is selected from the group consisting of a differentiating agent, a pharmaceutical and a hormone.

\* \* \* \* \*